United States Patent
Grapperhaus et al.

(10) Patent No.: US 6,465,686 B2
(45) Date of Patent: Oct. 15, 2002

(54) HALOGENATED 2-AMINO-5,6 HEPTENOIC ACID DERIVATIVES USEFUL AS NITRIC OXIDE SYNTHASE INHIBITORS

(75) Inventors: Margaret L. Grapperhaus, Troy, IL (US); James A. Sikorski, St. Louis, MO (US); Alok K. Awasthi, Skokie, IL (US); Lijuan J. Wang, Wildwood, MO (US); Barnett S. Pitzele, Skokie, IL (US); Donald W. Hansen, Jr., Skokie, IL (US); Pamela T. Manning, Labadie, MO (US)

(73) Assignee: Pharmacia Corporation, Skokie, IL (US)

(*) Notice: Subject to any disclaimer, the term of this patent is extended or adjusted under 35 U.S.C. 154(b) by 0 days.

(21) Appl. No.: 09/835,191

(22) Filed: Apr. 13, 2001

(65) Prior Publication Data

US 2002/0049202 A1 Apr. 25, 2002

Related U.S. Application Data

(60) Provisional application No. 60/197,032, filed on Apr. 13, 2000.

(51) Int. Cl.$^7$ ............................................. C07C 241/00
(52) U.S. Cl. ................. 562/439; 562/560; 562/507; 562/561; 562/540; 562/512; 562/602; 560/34; 560/125; 560/168; 560/172; 560/155; 564/193; 564/230; 514/613; 514/626; 514/627; 514/628; 514/631; 514/633
(58) Field of Search ............................... 562/561, 540, 562/512, 553, 598, 602, 605, 439, 560; 564/193, 204, 209, 225, 229; 514/613, 626, 627, 628, 631, 633; 560/155, 168, 172

(56) References Cited

U.S. PATENT DOCUMENTS

| | | | |
|---|---|---|---|
| 5,132,453 A | 7/1992 | Griffith | 562/560 |
| 5,684,008 A | 11/1997 | Hallinan et al. | 514/256 |
| 5,830,917 A | 11/1998 | Moore et al. | 514/634 |
| 5,854,251 A | 12/1998 | Hallinan et al. | 514/256 |
| 5,863,931 A | 1/1999 | Beams et al. | 514/357 |
| 5,919,787 A | 7/1999 | Hallinan et al. | 514/256 |
| 5,945,408 A | 8/1999 | Webber et al. | 514/63 |
| 5,981,511 A | 11/1999 | Gapud et al. | 514/63 |
| 5,994,391 A | 11/1999 | Lee et al. | 514/431 |
| 6,169,089 B1 | 1/2001 | Hallinan et al. | 514/256 |

FOREIGN PATENT DOCUMENTS

| | | | | |
|---|---|---|---|---|
| EP | 04 46699 | | 5/2000 | C07K/5/06 |
| EP | 05 21471 | | 10/2000 | C07D/239/42 |
| WO | WO 93 13055 | | 7/1993 | C07C/257/14 |
| WO | WO 93 16055 | | 8/1993 | C07D/281/10 |
| WO | WO 94 12165 | | 6/1994 | A61K/31/155 |
| WO | WO 94 14780 | | 7/1994 | C07D/239/48 |
| WO | WO 95 11014 | | 4/1995 | A61K/31/00 |
| WO | WO 95 11231 | | 4/1995 | C07D/207/22 |
| WO | WO 95/24382 | * | 9/1995 | C07C/254/14 |
| WO | WO 95 25717 | | 9/1995 | C07C/257/14 |
| WO | WO 96 15120 | | 5/1996 | C07D/257/06 |
| WO | WO 96 33175 | | 10/1996 | C07D/223/12 |
| WO | WO 96 35677 | | 11/1996 | C07D/223/12 |
| WO | WO 97 06802 | | 2/1997 | A61K/31/495 |
| WO | WO 99 29865 | | 6/1999 | C12N/15/28 |
| WO | WO 99 46240 | | 9/1999 | C07C/257/14 |

OTHER PUBLICATIONS

S. Moncada and E. Higgs, *Molecular Mechanisms and Therapeutic Strategies Related to Nitric Oxide* 1995, FASEB J., 9, 1319–1330.

S. Rozen, I. Shahak, and E. Bergmann, *Organic Fluorine Compounds Part XLIV. Preparation and Reactions of Epi–fluorohydrin* 1971, Synthesis 646–7.

E. Bergmann, S. Cohen, and I. Shahak, *Organic Fluorine Compounds. Part XX. Some Reactions of 1–Chloro–3–fluoropropan–2–ol and Epifluorohydrin* 1961, J Chem Soc 3448–52.

A. Jeanguenat and D. Seebach, *Stereoselective Chain Elongation at C–3 of Cysteine through 2,3–Dihydrothiazoles, Without Racemization. Preparation of 2–Amino–5–hydroxy–3–mercapto alkanoic Acid Derivatives.* 1991, J. Chem. Soc. Perkin Trans. 1, 2291–8.

G. Pattenden, S. Thom, and M. Jones, *Enantioselective Synthesis of 2–Alkyl Substituted Cysteines.* 1993, Tetrahedron, 49, 2131.

D. Bredt and S. Snyder, *Isolation of nitric oxide synthetase, a calmodulin–requiring enzyme.* 1990 Proc. Natl. Acad. Sci. U.S.A., 87, 682–685.

Moore et al, *2–Iminopiperidine and Other 2–Iminoazaheterocycles as Potent Inhibitors of Human Nitric Oxide Synthase Isoforms* 1996 J. Med. Chem., 39, 669–672.

T. Misko et al, *A Fluorometric Assay for the Measurement of Nitrite in Biological Samples* 1993, Analytical Biochemistry, 214, 11–16.

Y. Lee et al., *Conformationally–restricted Arginine Abalogues as Alternative Substrates and Inhibitors of Nitric Oxide Synthases* 1999 Bioorg. Med. Chem. 7 1097–1104.

R. Young et al . . , *Inhibition of Inducible Nitric Oxide Synthase by Acetamidine Derivatives of Hetero–Substituted Lysine and Homolysine* 2000 Bioorg. Med. Chem. Lett. 10 597–600.

* cited by examiner

*Primary Examiner*—Paul J. Killos
(74) *Attorney, Agent, or Firm*—Philip B. Polster, II

(57) ABSTRACT

The present invention discloses halogenated 2-amino-5,6 heptenoic acid derivatives useful as nitric oxide synthase inhibitors.

106 Claims, No Drawings

US 6,465,686 B2

HALOGENATED 2-AMINO-5,6 HEPTENOIC ACID DERIVATIVES USEFUL AS NITRIC OXIDE SYNTHASE INHIBITORS

CROSS REFERENCE TO RELATED APPLICATIONS

This application claims the benefit of U.S. Provisional Application Ser. No. 60/197,032, filed Apr. 13, 2000.

FIELD OF THE INVENTION

The present invention relates to halogenated amidino compounds and their use in therapy, in particular their use as nitric oxide synthase inhibitors.

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed, this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase, such consequences including hypertension and possible thrombosis and tissue damage. In particular, in the case of the therapeutic use of L-NMMA (a non-selective NO synthase inhibitor) for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

The following individual publications disclose compounds described as useful to inhibit nitric oxide synthesis and preferentially inhibit the inducible isoform of nitric oxide synthase:
International Publication No. WO 96/35677
International Publication No. WO 96/33175
International Publication No. WO 96/15120
International Publication No. WO 95/11014
International Publication No. WO 95/11231
International Publication No. WO 95/25717
International Publication No. WO 95/24382
International Publication No. WO94/12165
International Publication No. WO94/14780
International Publication No. WO93/13055
European Patent Application No. EP0446699A1
U.S. Pat. No. 5,132,453
U.S. Pat. No. 5,684,008
U.S. Pat. No. 5,830,917
U.S. Pat. No. 5,854,251
U.S. Pat. No. 5,863,931
U.S. Pat. No. 5,919,787
U.S. Pat. No. 5,945,408
U.S. Pat. No. 5,981,511
International Publication No.WO 95/25717 discloses certain amidino derivatives as being useful in inhibiting inducible nitric oxide synthase.

International Publication No. WO 99/62875 discloses further amidino compounds as being useful in inhibiting inducible nitric oxide synthase.

In particular International Publication No. WO 99/46240 discloses compounds said to be useful in inhibiting inducible nitric oxide synthase. Furthermore, International Publication No. WO 96/15120 discloses aminotetrazole derivative compounds described as useful in inhibiting inducible nitric oxide synthase.

Various attempts have been made to improve the potency and selectivity of NOS inhibitors by adding one or more rigidifying elements to the inhibitor'structure. A publications by Y. Lee et al (*Bioorg. Med. Chem.* 7, 1097 (1999)) teaches that imposing conformational rigidity with one or more carbon-carbon double bonds is not a favorable approach to impart selectivity for NOS inhibitors. This teaching is restated in R. J. Young et al (*Bioorg. Med. Chem. Lett.* 10, 597 (2000)).

SUMMARY OF THE INVENTION

Compounds are now disclosed which have the advantage of being very efficacious as iNOS inhibitors in the human cartilage explant assay, an in vitro model for osteoarthritis.

The present invention demonstrates that a halogenated carbon-carbon double bond can be utilized, and a carbon-carbon double bond may be used as a rigidifying element, with the resulting compounds having unexpected potency and selectivity for inhibition of inducible NOS.

Compounds of the present invention are unexpectedly potent and highly selective inhibitors of inducible nitric oxide synthase, and exhibit a relatively long half life in vivo. The compounds of the present invention may therefore optionally be administered efficaciously in divided doses, such as, for example, every other day or twice per week.

In a broad embodiment, the present invention is directed to novel compounds, pharmaceutical compositions and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

In one embodiment of the present invention, the compounds are provided having Formula I:

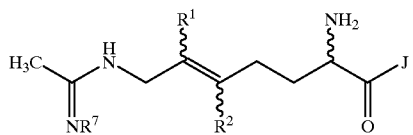

I or a pharmaceutically acceptable salt thereof, wherein:
$R^1$ is selected from the group consisting of H, halo and alkyl which may be optionally substituted by one or more halo;
$R^2$ is selected from the group consisting of H, halo and alkyl which may be optionally substituted by one or more halo;
with the proviso that at least one of $R^1$ or $R^2$ contains a halo;
$R^7$ is selected from the group consisting of H and hydroxy; and
J is selected from the group consisting of hydroxy, alkoxy, and $NR^3R^4$ wherein;
$R^3$ is selected from the group consisting of H, lower alkyl, lower alkylenyl and lower alkynyl; and
$R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Another embodiment of the present invention provides compounds having the Formula II:

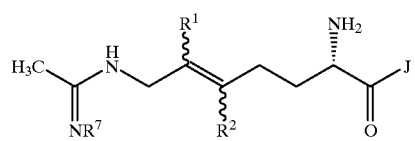

II or a pharmaceutically acceptable salt thereof, wherein:
$R^1$ is selected from the group consisting of H, halo and alkyl which may be optionally substituted by one or more halo;
$R^2$ is selected from the group consisting of H, halo and alkyl which may be optionally substituted by one or more halo;
with the proviso that at least one of $R_1$ or $R_2$ contains a halo;
$R^7$ is selected from the group consisting of H and hydroxy; and
J is selected from the group consisting of hydroxy, alkoxy, and $NR^3R^4$ wherein;
$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Yet another embodiment of the present invention provides compounds having the Formula III:

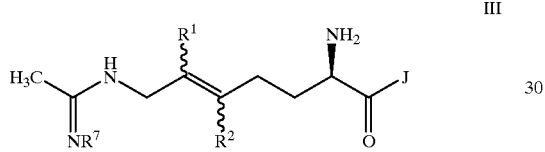

or a pharmaceutically acceptable salt thereof, wherein:
  $R^1$ is selected from the group consisting of H, halo and alkyl which is optionally substituted by one or more halo;
  $R^2$ is selected from the group consisting of H, halo and alkyl which may be optionally substituted by one or more halo;
with the proviso that at least one of $R^1$ or $R^2$ contains a halo;
$R^7$ is selected from the group consisting of H and hydroxy; and
  J is selected from the group consisting of hydroxy, alkoxy, and $NR^3R^4$ wherein;
  $R^3$ is selected from the group consisting of H, lower alkyl, lower alkylenyl and lower alkynyl; and
  $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

A particularly preferred embodiment of the present invention provides compounds having the Formula IV:

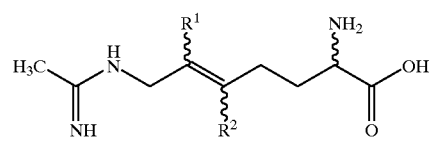

or a pharmaceutically acceptable salt thereof, wherein;
  $R^1$ is selected from the group consisting of H, halo and alkyl which may be optionally substituted by one or more halo; and
  $R^2$ is selected from the group consisting of H, halo and alkyl which may be optionally substituted by one or more halo;
with the proviso that at least one of $R^1$ or $R^2$ contains a halo.

Another particularly preferred embodiment of the present invention provides compounds having the Formula V:

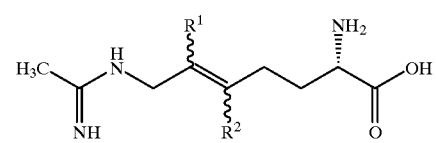

or a pharmaceutically acceptable salt thereof, wherein:
  $R^1$ is selected from the group consisting of H, halo and alkyl which may be optionally substituted by one or more halo; and
  $R^2$ is selected from the group consisting of H, halo and alkyl which may be optionally substituted by one or more halo;
with the proviso that at least one of $R^1$ or $R^2$ contains a halo.

Another highly preferred embodiment of the invention provides compounds having the Formula VI:

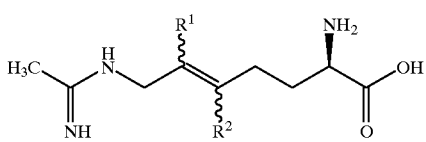

VI or a pharmaceutically acceptable salt thereof, wherein:
$R^1$ is selected from the group consisting of H, halo and alkyl which may be optionally substituted by one or more halo; and
$R^2$ is selected from the group consisting of H, halo and alkyl which may be optionally substituted by one or more halo;
with the proviso that at least one of $R^1$ or $R^2$ contains a halo.

The present invention also includes pharmaceutical compositions which comprise a compound of Formulas I, II, III, IV, V or VI.

Another aspect of the present invention is the novel intermediate compound used in the preparation of the therapeutic compounds of the present invention, represented by formula VII

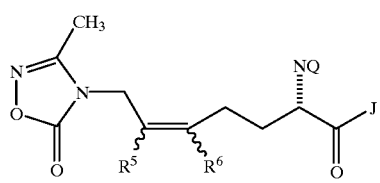

VII wherein $R^5$ is selected from the group consisting of H, F, and methyl;
$R^6$ is selected from the group consisting of H, F, and methyl; with the proviso that either $R^5$ or $R^6$ must be F.
J is selected from the group consisting of hydroxy, alkoxy; and $NR^3R^4$ where $R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Q is H, or an appropriate nitrogen protecting moiety such as, for example, t-butoxycarbonyl, 2-(4-biphenylyl) propyl (2)oxycarbonyl (Bpoc), 2-nitro-phenylsulfenyl (Nps) or dithia-succionyl.

DETAILED DESCRIPTION OF THE INVENTION

The present invention provides compounds having a halogenated carbon-carbon double bond, and these compounds have unexpected greater potency and selectivity for inhibition of inducible NOS.

Compounds of the present invention are unexpectedly potent and highly selective inhibitors of inducible nitric oxide synthase, and exhibit a relatively long half life in vivo as compared with known nitric oxide synthase inhibitors.

Compounds of Formulas I, II, III, IV, V and VI will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID, opioid analgesic or certain anti-convulsants would traditionally be administered.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temperoramandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents. The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofirin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89- A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23–112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-

104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid).

A further embodiment provides a therapeutic combination of a compound of the present invention with an opioid compound. Opioid compounds useful in this combination include without limitation morphine, methadone, hydromorphone, oxymorphone, levorphanol, levallorphan, codeine,dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-1a$^2$, glu$^4$]deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

The term "alkyl", alone or in combination, means an acyclic alkyl radical, linear or branched, preferably containing from 1 to about 10 carbon atoms, more preferably containing from 1 to about 6 carbon atoms, and still more preferably about 1 to 3 carbon atoms. "Alkyl" also encompasses cyclic alkyl radicals containing from 3 to about 7 carbon atoms, preferably from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. Said alkenyl radicals may be optionally substituted with groups as defined below. Examples of suitable alkenyl radicals include propenyl, 2-chloropropylenyl, buten-1-yl, isobutenyl, penten-1-yl, 2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "alkoxy" embrace linear or branched oxy-containing radicals each having alkyl portions of 1 to about 6 carbon atoms, preferably 1 to about 3 carbon atoms, such as a methoxy radical. The term "alkoxyalkyl" also embraces alkyl radicals having one or more alkoxy radicals attached to the alkyl radical, that is, to form monoalkoxyalkyl and dialkoxyalkyl radicals. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylthio" embraces radicals containing a linear or branched alkyl radical, of 1 to about 6 carbon atoms, attached to a divalent sulfur atom. An example of "lower alkylthio" is methylthio ($CH_3$—S—).

The term "alkylthioalkyl" embraces alkylthio radicals, attached to an alkyl group. Examples of such radicals include methylthiomethyl.

The term "halo" means halogens such as fluorine, chlorine, bromine or iodine atoms. The term "heterocyclyl" means a saturated or unsaturated mono- or multi-ring carbocycle wherein one or more carbon atoms is replaced by N, S, P, or O. This includes, for example, the following structures:

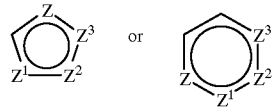

wherein Z, $Z^1$, $Z^2$ or $Z^3$ is C, S, P, O, or N, with the proviso that one of Z, $Z^1$, $Z^2$ or $Z^3$ is other than carbon, but is not O or S when attached to another Z atom by a double bond or when attached to another O or S atom. Furthermore, the optional substituents are understood to be attached to Z, $Z^1$, $Z^2$ or $Z^3$ only when each is C. The term "heterocyclyl" also includes fully saturated ring structures such as piperazinyl, dioxanyl, tetrahydrofuranyl, oxiranyl, aziridinyl, morpholinyl, pyrrolidinyl, piperidinyl, thiazolidinyl, and others. The term "heterocyclyl" also includes partially unsaturated ring structures such as dihydrofuranyl, pyrazolinyl, imidazolinyl, pyrrolinyl, chromanyl, dihydrothiophenyl, and others.

The term "heteroaryl" means a fully unsaturated heterocycle.

In either "heterocycle" or "heteroaryl," the point of attachment to the molecule of interest can be at the heteroatom or elsewhere within the ring.

The term "cycloalkyl" means a mono- or multi-ringed carbocycle wherein each ring contains three to about seven carbon atoms, preferably three to about five carbon atoms. Examples include radicals such as cyclopropyl, cyclobutyl, cyclopentyl, cyclohexyl, cycloalkenyl, and cycloheptyl. The term "cycloalkyl" additionally encompasses spiro systems.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Examples of such radicals include methoxy, ethoxy, propoxy, isopropoxy, butoxy and tert-butoxy.

The term "aryl" means a fully unsaturated mono- or multi-ring carbocycle, including, but not limited to, substituted or unsubstituted phenyl, naphthyl, or anthracenyl.

The term "combination therapy" means the administration of two or more therapeutic agents to treat a therapeutic condition or disorder described in the present disclosure, for example atherosclerosis, pain, inflammation, migraine, neoplasia, angiogenisis-related condition or disorder, or other. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to include and qualify a combined amount of active ingredients in a combination therapy. This combined amount will achieve the goal of ameliorating the symptoms of, reducing or eliminating the targeted condition.

In one embodiment, the present invention provides a compound or a salt thereof, the compound having a structure corresponding to Formula 1:

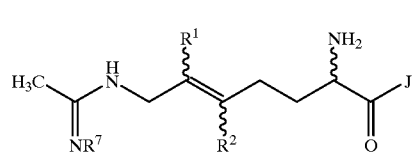

or a pharmaceutically acceptable salt thereof, wherein:

$R^1$ is selected from the group consisting of H, halo and alkyl which is optionally substituted by one or more halo;

$R^2$ is selected from the group consisting of H, halo and alkyl which is optionally substituted by one or more halo;

with the proviso that at least one of $R^1$ or $R^2$ contains a halo;

$R^7$ is selected from the group consisting of H and hydroxy; and

J is selected from the group consisting of hydroxy, alkoxy, and $NR^3R^4$ wherein;

$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Formula I may also be represented wherein:
$R^1$ is selected from the group consisting of H and $C_1$–$C_3$ alkyl which may be optionally substituted by one or more halo, and
$R^2$ is fluorine.

Further, Formula I may be represented wherein:
$R^1$ is H; and
$R^2$ is fluorine.

Formula I may also be represented by compounds wherein:
$R^1$ is halo; and
$R^2$ is halo.

Further, Formula I may be represented wherein:
$R^1$ is fluorine; and
$R^2$ is selected from the group consisting of H and $C_1$–$C_3$ alkyl which may be optionally substituted by one or more halo.

Formula I may also be represented by compounds wherein:
$R^1$ is fluorine; and
$R^2$ is H.

Further, Formula I may be represented by compounds wherein:
$R^1$ is fluorine; and
$R^2$ is fluorine.

Formula I may be represented wherein the compound is the E isomer.

In another embodiment of the present invention, the compounds are represented by Formula II:

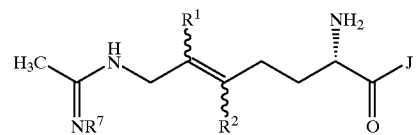

or a pharmaceutically acceptable salt thereof, wherein:
$R^1$ is selected from the group consisting of H, halo and alkyl which is optionally substituted by one or more halo;
$R^2$ is selected from the group consisting of H, halo and alkyl which is optionally substituted by one or more halo;
with the proviso that at least one of $R_1$ or $R_2$ contains a halo;
$R^7$ is selected from the group consisting of H and hydroxy; and
J is selected from the group consisting of hydroxy, alkoxy, and $NR^3R^4$ wherein;
$R^3$ is selected from the group consisting of H, lower alkyl, lower alkylenyl and lower alkynyl; and
$R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Formula II may also be represented wherein:
$R^1$ is fluorine; and
$R^2$ is selected from the group consisting of H and $C_1$–$C_3$ alkyl which is optionally substituted by one or more halo.

Another embodiment of the invention is Formula II wherein:
$R^1$ is H; and
$R^2$ is fluorine.

The compounds of Formula II may also be represented wherein:
$R^1$ is selected from the group consisting of H, halo and alkyl which is optionally substituted by one or more halo; and
$R^2$ is halo.

Another embodiment of the invention is Formula II wherein:
$R^1$ is selected from the group consisting of H, fluorine and $C_1$–$C_3$ alkyl which is optionally substituted by one or more halo; and
$R^2$ is halo.

Formula II may also be represented wherein:
$R^1$ is selected from the group consisting of H and $C_1$–$C_3$ alkyl which is optionally substituted by one or more halo; and
$R^2$ is fluorine.

Further, Formula II may be represented wherein:
$R^1$ is H; and
$R^2$ is fluorine.

Formula II may also be represented by compounds wherein:
$R^1$ is halo; and
$R^2$ is halo.

Formula II may also be represented wherein:
$R^1$ is fluorine; and
$R^2$ is H

Further, Formula II may be represented by compounds wherein:
$R^1$ is fluorine; and
$R^2$ is fluorine.

Formula II may be represented wherein the compound is the E isomer.

In yet another embodiment of the present invention, the compounds are represented by Formula III:

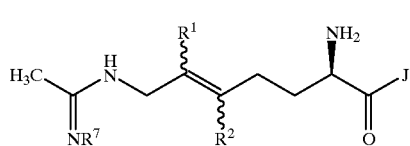

III or a pharmaceutically acceptable salt thereof, wherein:
$R^1$ is selected from the group consisting of H, halo and alkyl which is optionally substituted by one or more halo;
$R^2$ is selected from the group consisting of H, halo and alkyl which is optionally substituted by one or more halo;
with the proviso that at least one of $R^1$ or $R^2$ contains a halo;
$R^7$ is selected from the group consisting of H and hydroxy; and
J is selected from the group consisting of hydroxy, alkoxy, and $NR^3R^4$ wherein;

$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

In another embodiment of Formula III, the compounds are represented wherein:
$R^1$ is halo; and
$R^2$ is selected from the group consisting of H, halo and alkyl which is optionally substituted by one or more halo.

In another embodiment, the compounds are represented by Formula III wherein:
$R^1$ is halo; and
$R^2$ is selected from the group consisting of H, fluorine and $C_1$–$C_3$ alkyl which is optionally substituted by one or more halo.

Formula III may also be represented wherein:
$R^1$ is fluorine; and
$R^2$ is selected from the group consisting of H and $C_1$–$C_3$ alkyl which is optionally substituted by one or more halo.

Another embodiment of the invention is Formula III wherein:
$R^1$ is fluorine; and
$R^2$ is H.

Formula III may also be represented wherein:
$R^1$ is selected from the group consisting of H, halo and alkyl which is optionally substituted by one or more halo; and
$R^2$ is halo.

Another embodiment of the invention is Formula III wherein:
$R^1$ is selected from the group consisting of H, fluorine and $C_1$–$C_3$ alkyl which is optionally substituted by one or more halo; and
$R^2$ is halo.

Formula III may also be represented wherein:
$R^1$ is selected from the group consisting of H and $C_1$–$C_3$ alkyl which is optionally substituted by one or more halo; and
$R^2$ is fluorine.

Further, compounds of the invention may be represented by Formula III wherein:
$R^1$ is H; and
$R^2$ is fluorine.

Formula III may also be represented by compounds wherein:
$R^1$ is halo; and
$R^2$ is halo.

Further, Formula III may be represented by compounds wherein:
$R^1$ is fluorine; and
$R^2$ is selected from the group consisting of H and $C_1$–$C_3$ alkyl which is optionally substituted by one or more halo.

Further, Formula III may be represented by compounds wherein:
$R^1$ is fluorine; and
$R^2$ is fluorine.

Formula III may be represented wherein the compound is the E isomer.

In a particularly preferred embodiment of the present invention, the compounds are represented by Formula IV:

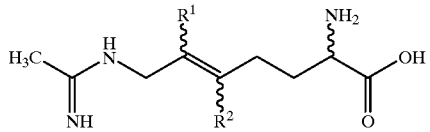

IV or a pharmaceutically acceptable salt thereof, wherein;
$R^1$ is selected from the group consisting of H, halo and alkyl which is optionally substituted by one or more halo;
$R^2$ is selected from the group consisting of H, halo and alkyl which may be optionally substituted by one or more halo; and
with the proviso that at least one of $R^1$ or $R^2$ contains a halo.

In another embodiment of Formula IV, the compounds are represented wherein:
$R^1$ is halo; and
$R^2$ is selected from the group consisting of H, halo and alkyl which is optionally substituted by one or more halo.

In another embodiment the compounds are represented by Formula IV wherein:
$R^1$ is halo; and
$R^2$ is selected from the group consisting of H, fluorine and $C_1$–$C_3$ alkyl which is optionally substituted by one or more halo.

Formula IV may also be represented wherein:
$R^1$ is fluorine; and
$R^2$ is selected from the group consisting of H and $C_1$–$C_3$ alkyl which is optionally substituted by one or more halo.

Another embodiment of the invention is Formula IV wherein:
$R^1$ is fluorine; and
$R^2$ is H.

The compounds of Formula IV may also be represented wherein:
$R^1$ is selected from the group consisting of H, halo and alkyl which is optionally substituted by one or more halo; and
$R^2$ is halo.

Another embodiment of the invention is Formula IV wherein:
$R^1$ is selected from the group consisting of H, fluorine and $C_1$–$C_3$ alkyl which is optionally substituted by one or more halo; and
$R^2$ is halo.

Formula IV may also be represented wherein:
$R^1$ is selected from the group consisting of H and $C_1$–$C_3$ alkyl which is optionally substituted by one or more halo; and
$R^2$ is fluorine.

Further, Formula IV may be represented wherein:
$R^1$ is H; and
$R^2$ is fluorine.

Formula IV may also be represented by compounds wherein:
$R^1$ is halo; and
$R^2$ is halo.

Further, Formula IV may be represented by compounds wherein:
$R^1$ is fluorine; and
$R^2$ is fluorine.

Formula IV may be represented wherein the compound is the E isomer.

In another particularly preferred embodiment of the present invention, the compounds are represented by Formula V:

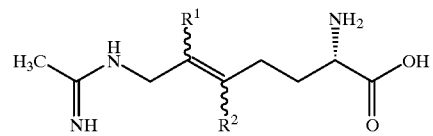

V or a pharmaceutically acceptable salt thereof, wherein:
$R^1$ is selected from the group consisting of H, halo and alkyl which may be optionally substituted by one or more halo;
$R^2$ is selected from the group consisting of H, halo and alkyl which may be optionally substituted by one or more halo; and
with the proviso that at least one of $R^1$ or $R^2$ contains a halo.

In another embodiment of Formula V, the compounds are represented wherein:
$R^1$ is halo; and
$R^2$ is selected from the group consisting of H, halo and alkyl which is optionally substituted by one or more halo.

In another embodiment, the compounds are represented by Formula V wherein:
$R^1$ is halo; and
$R^2$ is selected from the group consisting of H, fluorine and $C_1$–$C_3$ alkyl which is optionally substituted by one or more halo.
Formula V may also be represented wherein:
$R^1$ is fluorine; and
$R^2$ is selected from the group consisting of H and $C_1$–$C_3$ alkyl which is optionally substituted by one or more halo.
Another embodiment of the invention is Formula V wherein:
$R^1$ is fluorine; and
$R^2$ is H.
The compounds of Formula V may also be represented wherein:
$R^1$ is selected from the group consisting of H, halo and alkyl which is optionally substituted by one or more halo; and
$R^2$ is halo.
Another embodiment of the invention is Formula V wherein:
$R^1$ is selected from the group consisting of H, fluorine and $C_1$–$C_3$ alkyl which is optionally substituted by one or more halo; and
$R^2$ is halo.
Formula V may also be represented wherein:
$R^1$ is selected from the group consisting of H and $C_1$–$C_3$ alkyl which is optionally substituted by one or more halo; and
$R^2$ is fluorine.
Further, Formula V may be represented wherein:
$R^1$ is H; and
$R^2$ is fluorine.
Formula V may also be represented by compounds wherein:
$R^1$ is halo; and
$R^2$ is halo.
Further, Formula V may be represented by compounds wherein:
$R^1$ is fluorine; and
$R^2$ is fluorine.
Formula V may be represented wherein the compound is the E isomer.
In another highly preferred embodiment of the invention, the compounds are represented by Formula VI:

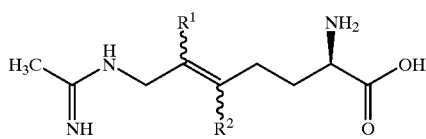

VI or a pharmaceutically acceptable salt thereof, wherein:
$R_1$ is selected from the group consisting of H, halo and alkyl which is optionally substituted by one or more halo;

$R^2$ is selected from the group consisting of H, halo and alkyl which is optionally substituted by one or more halo; and
with the proviso that at least one of $R^1$ or $R^2$ contains a halo.
In another embodiment of Formula VI, the compounds are represented wherein:
$R^1$ is halo; and
$R^2$ is selected from the group consisting of H, halo and alkyl which is optionally substituted by one or more halo.
In another embodiment, the compounds are represented by Formula VI wherein:
$R^1$ is halo; and
$R^2$ is selected from the group consisting of H, fluorine and $C_1$–$C_3$ alkyl which is optionally substituted by one or more halo.
Formula VI may also be represented wherein:
$R^1$ is fluorine; and
$R^2$ is selected from the group consisting of H and $C_1$–$C_3$ alkyl which is optionally substituted by one or more halo.
Another embodiment of the invention is Formula VI wherein:
$R^1$ is fluorine; and
$R^2$ is H.
The compounds of Formula VI may also be represented wherein:
$R^1$ is selected from the group consisting of H, halo and alkyl which is optionally substituted by one or more halo; and
$R^2$ is halo.
Another embodiment of the invention is Formula VI wherein:
$R^1$ is selected from the group consisting of H, fluorine and $C_1$–$C_3$ alkyl which is optionally substituted by one or more halo; and
$R^2$ is halo.
Formula VI may also be represented wherein:
$R^1$ is selected from the group consisting of H and $C_1$–$C_3$ alkyl which is optionally substituted by one or more halo; and
$R^2$ is fluorine.
Further, Formula VI may be represented wherein:
$R^1$ is H; and
$R^2$ is fluorine.
Formula VI may also be represented by compounds wherein:
$R^1$ is halo; and
$R^2$ is halo.
Further, Formula VI may be represented by compounds wherein:
$R^1$ is fluorine; and
$R^2$ is fluorine.
Formula VI may be represented wherein the compound is the E isomer.
When $R^1$ and $R^2$ are both represented by halogen in Formulas I, II, III, IV, V or VI, the compound can be either the E or Z isomer but preferably the Z isomer
The present invention also includes pharmaceutical compositions which comprise a compound of Formulas I, II, III, IV, V or VI.
The term "pharmaceutically-acceptable salts" embraces salts commonly used to form alkali metal salts and to form addition salts of free acids or free bases. The nature of the salt is not critical, provided that it is pharmaceutically acceptable. Pharmaceutically acceptable salts are particularly useful as products of the methods of the present invention because of their greater aqueous solubility relative to a corresponding parent or neutral compound. Such salts must have a pharmaceutically acceptable anion or cation. Suitable pharmaceutically-acceptable acid addition salts of compounds of the present invention may be prepared from inorganic acid or from an organic acid. Examples of such inorganic acids are hydrochloric, hydrobromic, hydroiodic, nitric, carbonic, sulfuric and phosphoric acid. Appropriate organic acids include from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. Suitable pharmaceutically acceptable acid addition salts of the compounds of the present invention when possible include those derived from inorganic acids, such as hydrochloric, hydrobromic, boric, fluoroboric, phosphoric, metaphosphoric, nitric, carbonic (including carbonate and hydrogen carbonate anions), sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable pharmaceutically acceptable base salts include ammonium salts, alkali metal salts such as sodium and potassium salts, and alkaline earth salts such as magnesium and calcium salts. All of these salts may be prepared by conventional means from the corresponding conjugate base or conjugate acid of the compounds of the present invention by reacting, respectively, the appropriate acid or base with the conjugate base or conjugate acid of the compound. Another pharmaceutically acceptable salt is a resin-bound salt.

While it may be possible for the compounds of the present invention to be administered as the raw chemical, it is preferable to present them as a pharmaceutical composition. According to a further aspect, the present invention provides a pharmaceutical composition comprising a compound of the present invention or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of The present invention or a pharmaceutically acceptable salt or solvate thereof with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 20 mg/kg per day. The dose range for adult humans is generally from 0.005 mg to 1 g/day. Tablets or other forms of presentation provided in discrete units may conveniently contain an amount of compound of the invention which is effective at such dosage or as a multiple of the same, for instance, units containing 5 mg to 50 mg, usually around 1 mg to 20mg.

The compounds of Formulas I, II, III, IV, V, and VI are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, isomers, the racemic mixtures thereof and other mixtures thereof, as falling within the scope of the invention. Pharmaceutically acceptable salts of such tautomeric, geometric or stereoisomeric forms are also included within the scope of the invention.

The terms "cis" and "trans" denote a form of geometric isomerism in which two carbon atoms connected by a double bond will each have two highest ranking groups on the same side of the double bond ("cis") or on opposite sides of the double bond ("trans"). Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

The following schemes are useful in making the present invention. As used in the preceding schemes, the following terms and abbreviations apply:

"Boc" means t-butoxycarbonyl;

"p-TsOH" means p-toluenesofonic acid;

Scheme 1

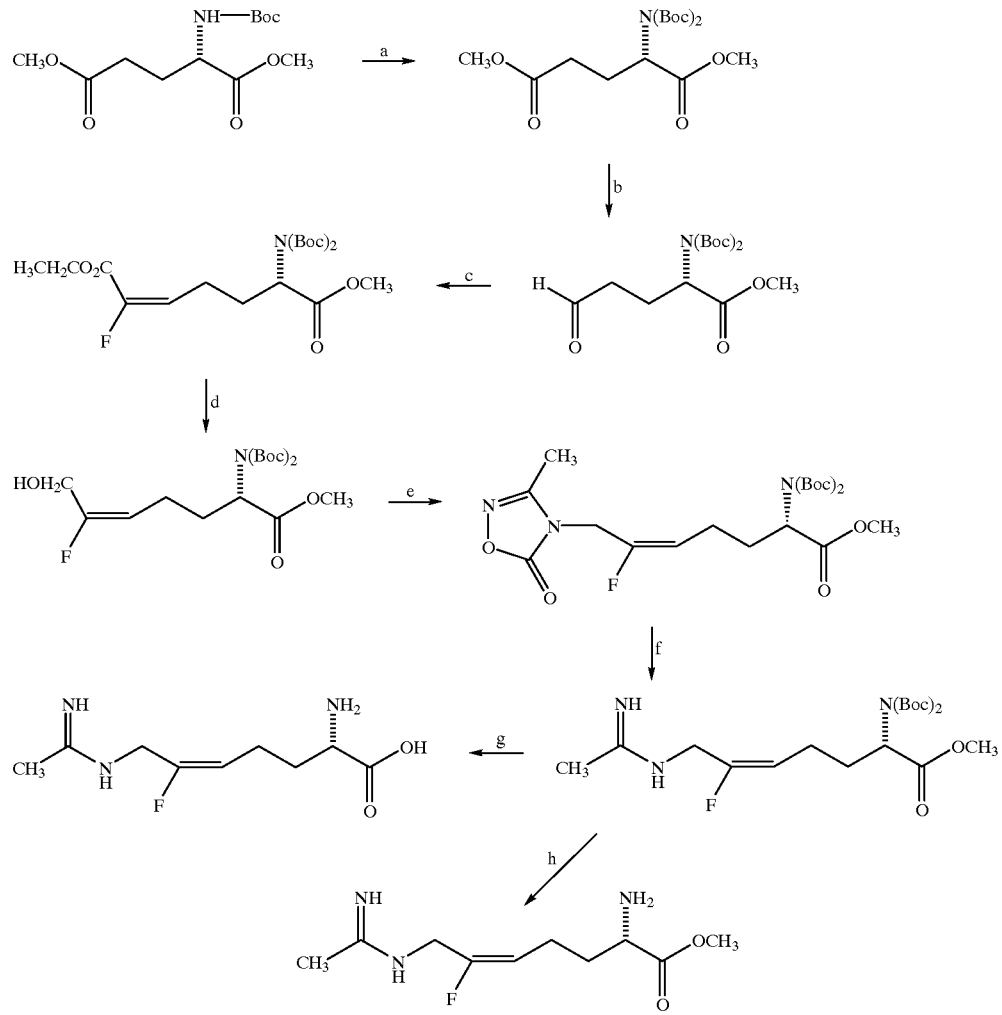

a) di-tert-butyldicarbonate, 4-dimethylaminopyridine, acetonitrile
b) DIBAL, hexane and diethyl ether
c) triethyl 2-fluorophosphonoacetate, n-butyl lithium, THF and hexane
d) $NaBH_4$, methanol
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl, heat
h) HCl•dioxane, HOAc, room temperature Scheme 2
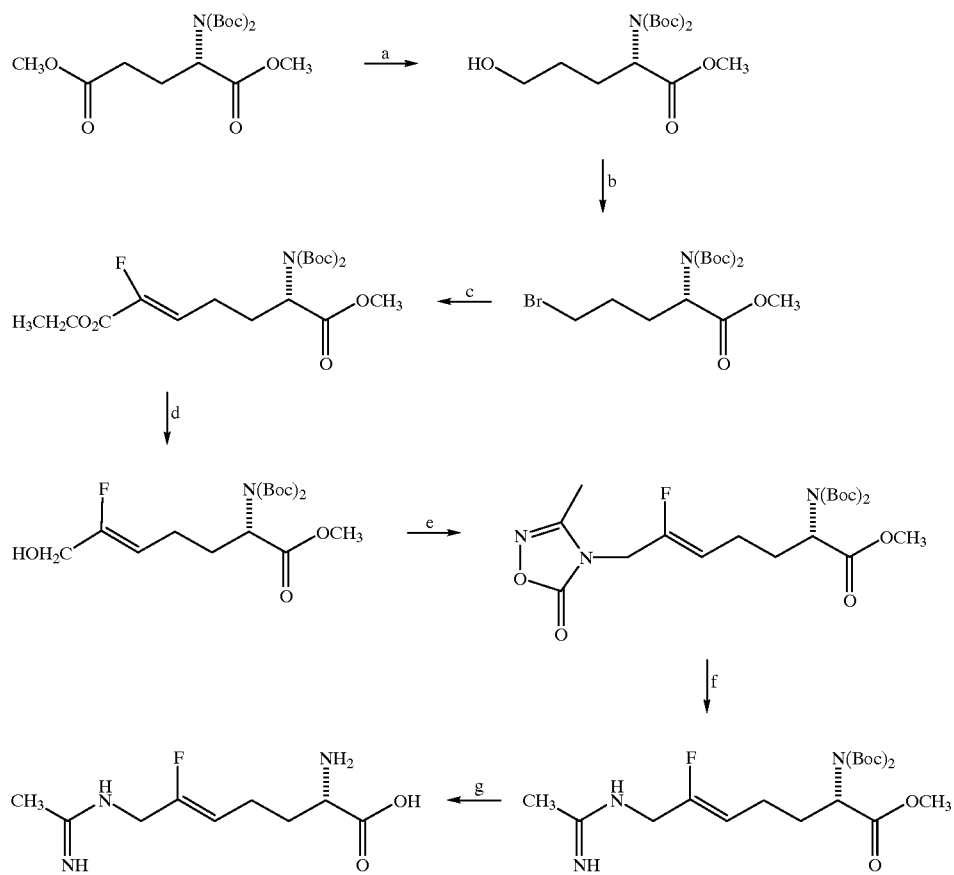
a) NaBH$_4$, methanol
b) carbon tetrabromide, THF, polymer-supported triphenylphosphine,
c) sodium hydride, DMF, ethyl fluoro[(4-methoxyphenyl)sulfinyl]acetate; heat
d) NaBH$_4$, methanol
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl, heat
Scheme 3
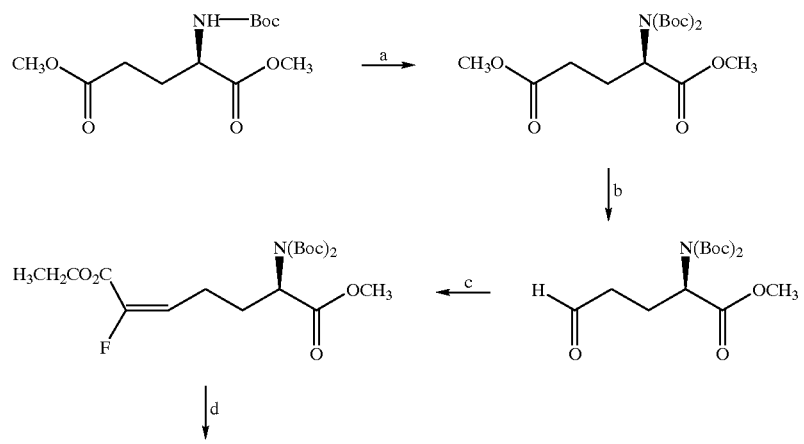

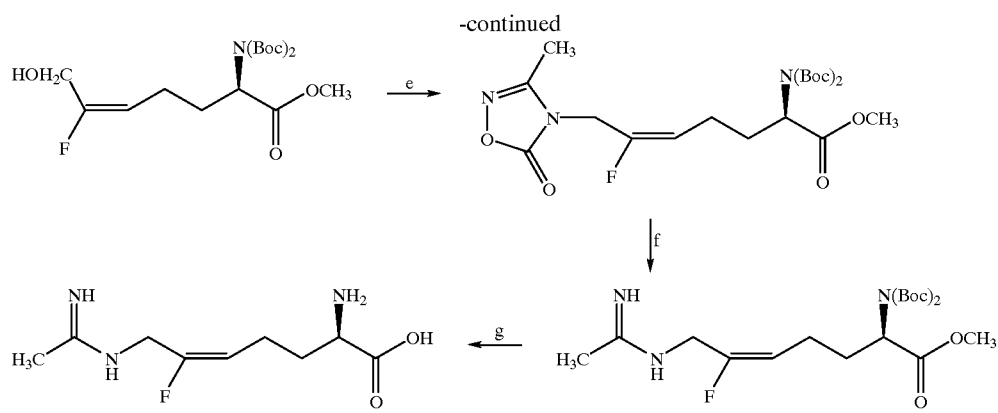

a) di-tert-butyldicarbonate, 4-dimethylaminopyridine, acetonitrile
b) DIBAL, hexane and diethyl ether
c) triethyl 2-fluorophosphonoacetate, n-butyl lithium, THF and hexane
d) NaBH$_4$, methanol
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl, heat Scheme 4

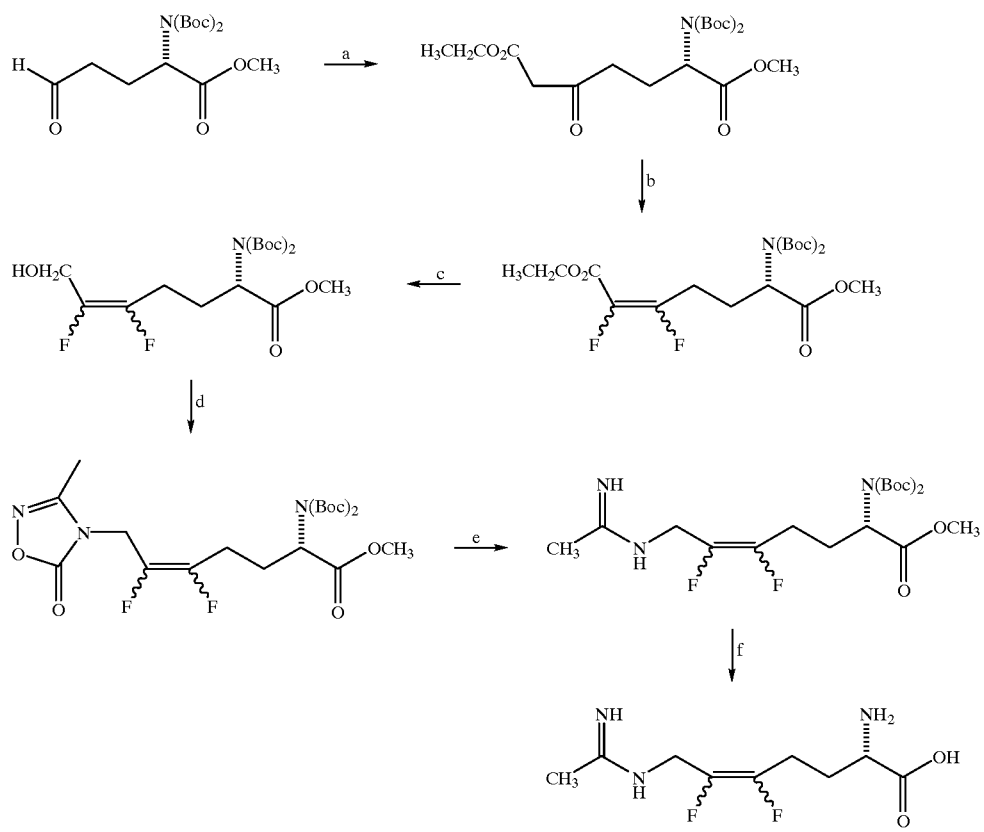

a) ethyl diazoacetate, tin(II) chloride, methylene chloride
b) DAST, N-methyl-2-pyrolidinone
c) NaBH$_4$, methanol
d) polymer-supported triphenylphosphine, 3-methyl-1,2,4-oxadiazolin-5-one, dimethylazodicarboxylate, THF
e) Zinc dust, methanol, acetic acid, water, sonification
f) aqueous HCl, heat Scheme 5
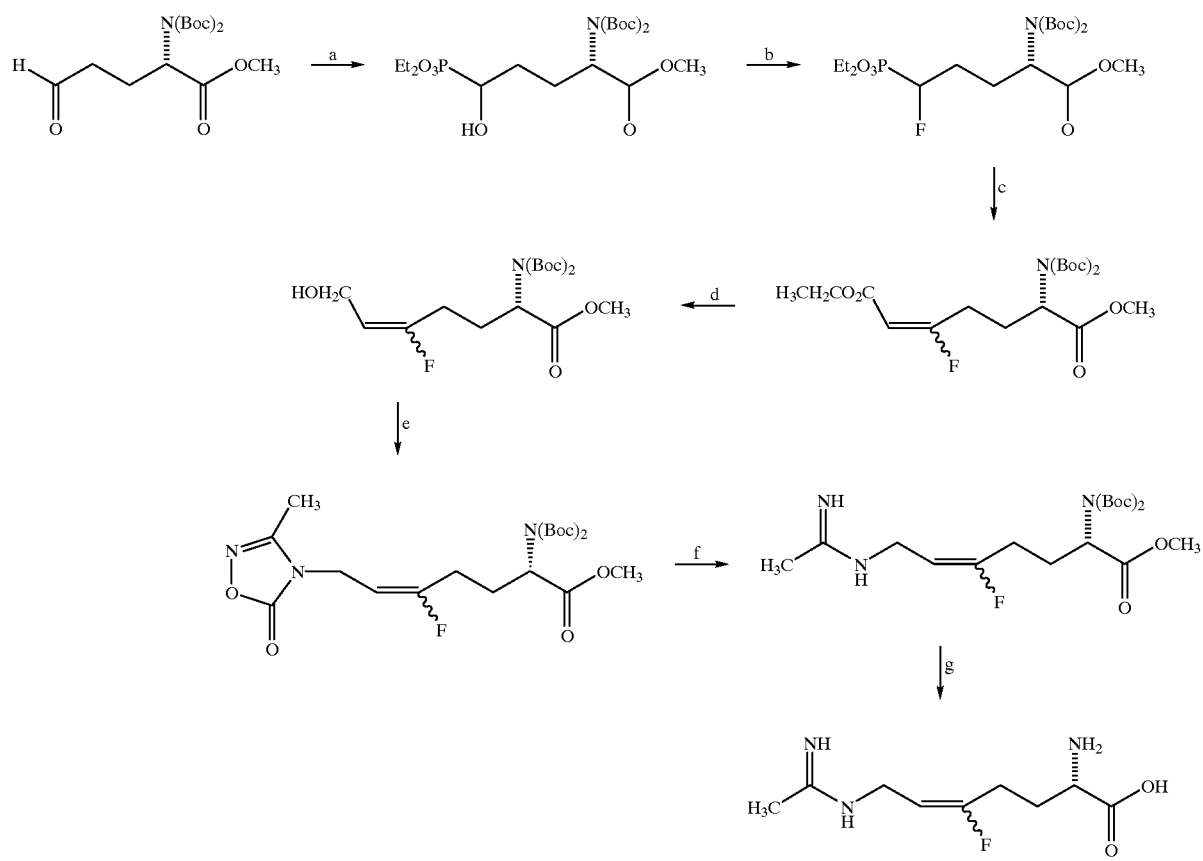
a) (EtO)$_2$POSiMe$_3$, heat, p-TsOH
b) DAST
c) n-butyl lithium, THF and hexane; ethyl glyoxalate
d) NaBH$_4$, methanol
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl
Scheme 6
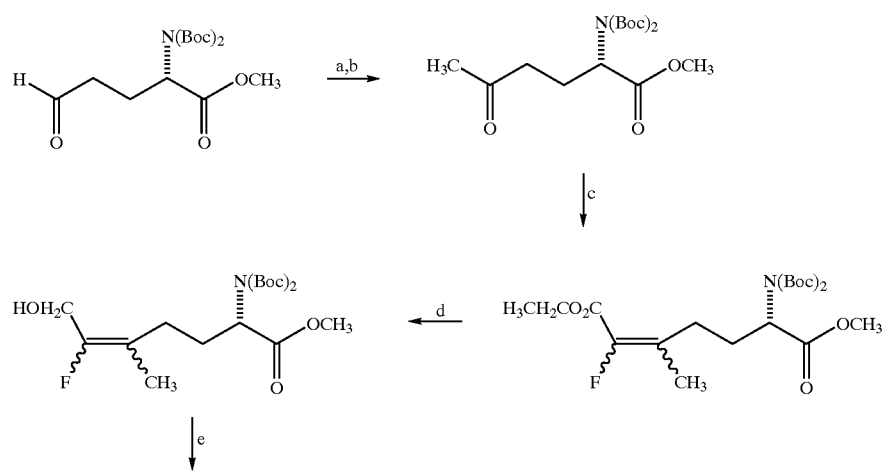

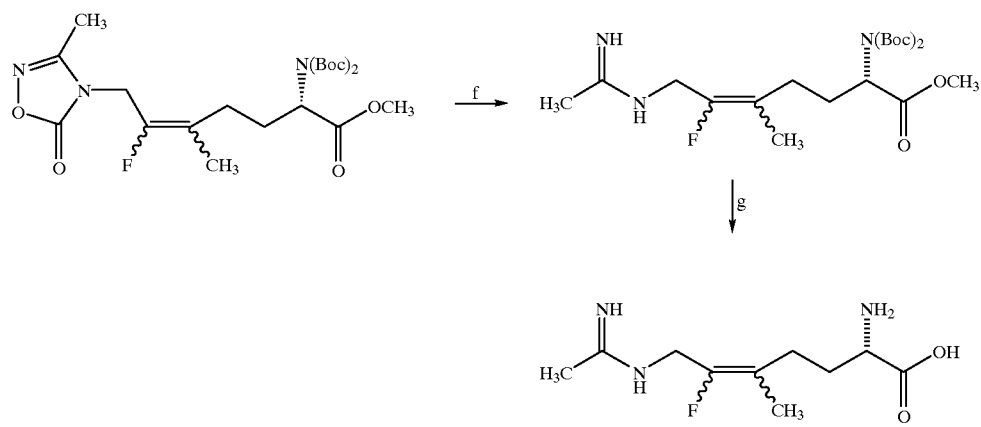

a) methyl Grignard, THF
b) N-methylmorpholine-N-oxide, tetra-n-propylammonium perruthenate, methylene chloride
c) triethyl 2-fluorophosphonoacetate, n-butyl lithium, THF and hexane
d) NaBH$_4$, methanol
e) polymer-supported triphenylphosphine, 3-methyl-1,2,4-oxadiazolin-5-one, dimethylazodicarboxylate, THF
f) Zinc dust, methanol, acetic acid, water, sonication
g) aqueous HCl, heat Scheme 7

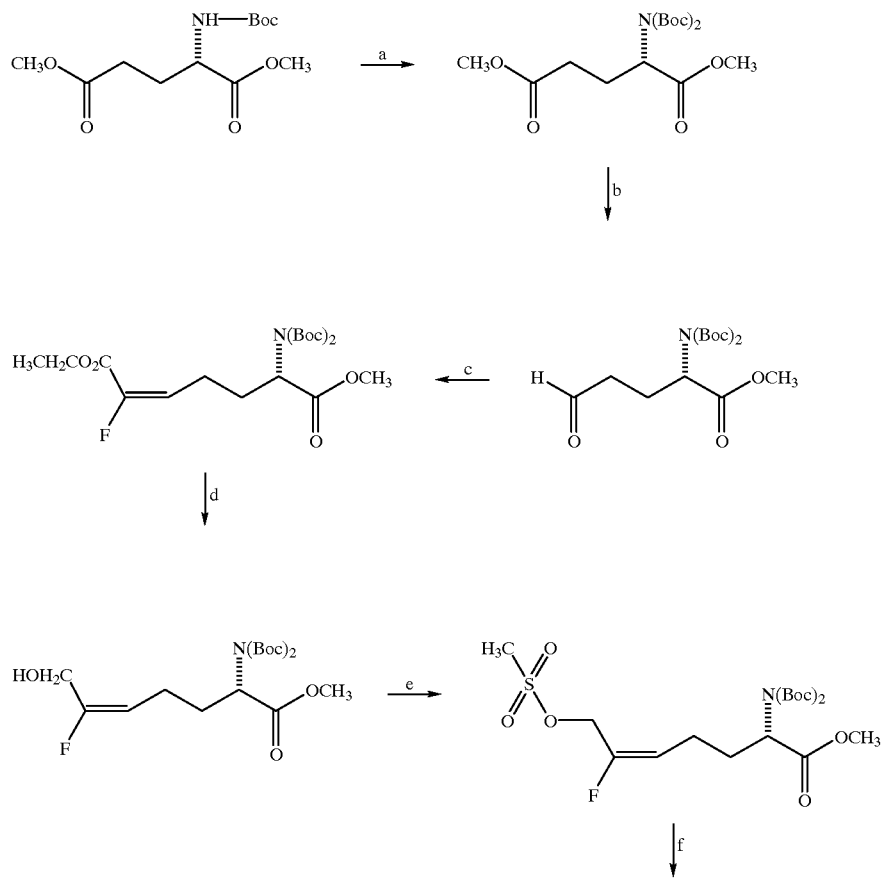

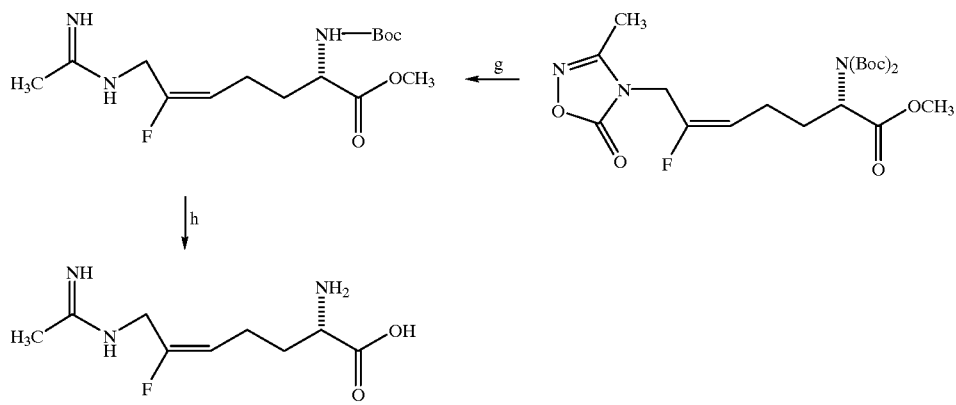

a) di-tert-butyldicarbonate, 4-dimethylaminopyridine, acetonitrile
b) DIBAL, hexane and diethyl ether
c) triethyl 2-fluorophosphonoacetate, n-butyl lithium, THF and hexane
d) Red-Al, THF
e) methanesulfonyl chloride, triethylamine, methylene chloride
f) potassium 3-methyl-1,2,4-oxadiazolin-5-onate, dimethyl formamide
g) Zinc dust, methanol, acetic acid, water, heat
h) aqueous HCl, heat Scheme 8

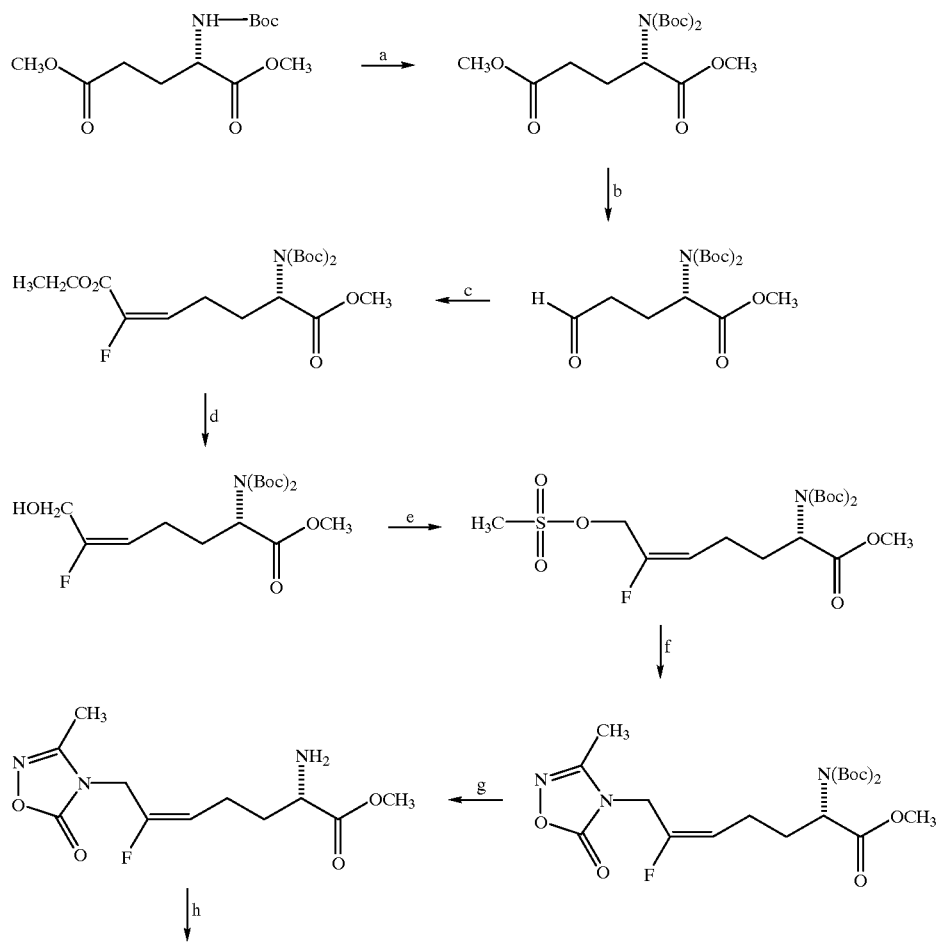

-continued

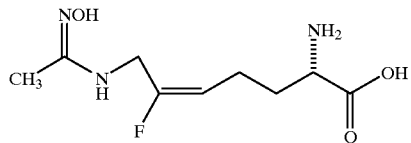

a) di-tert-butyldicarbonate, 4-dimethylaminopyridine, acetonitrile
b) DIBAL, hexane and diethyl ether
c) triethyl 2-fluorophosphonoacetate, n-butyl lithium, THF and hexane
d) NaBH$_4$, methanol
e) methane sulfonyl chloride, triethylamine, methylene chloride
f) potassium 3-methyl-1,2,4-oxadiazolin-5-onate, DMF
f) gaseous HCl, methanol
ha) aqueous NaOH, room temperature
hb) aqueous HCl Scheme 9

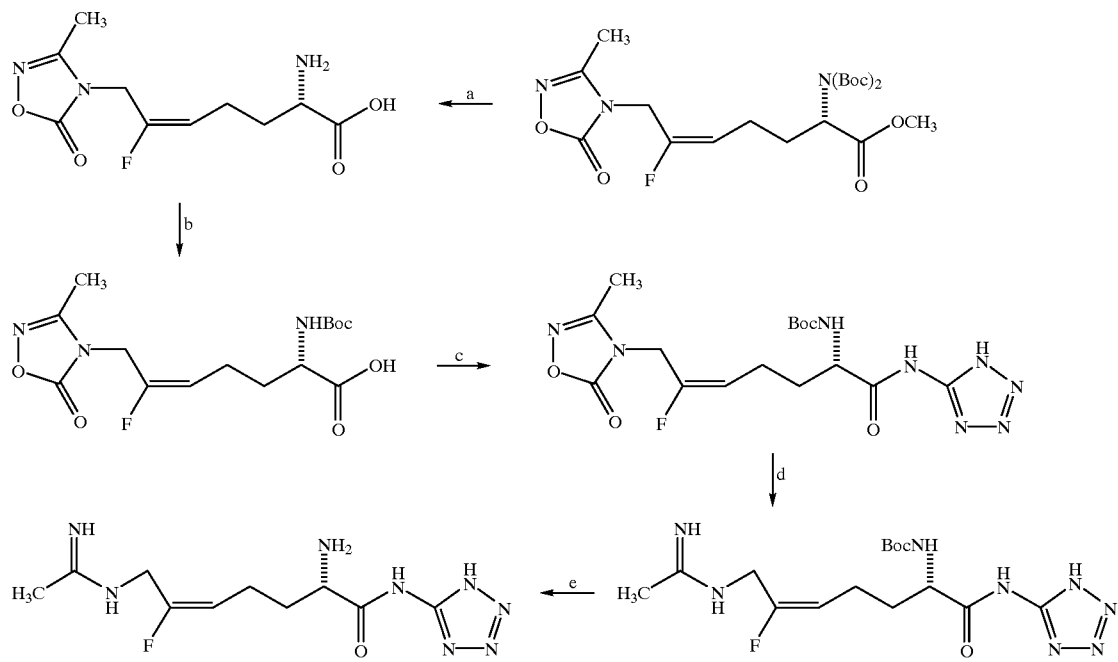

a) aqueos HCl, methanol, heat
b) di-tert-butyldicarbonate, triethylamine, dioxane, water
c) 5-aminotetrazole monohydrate, 1,3-diisopropylcarbodiimide, THF
d) Zinc dust, methanol, acetic acid, water, heat
e) HCl in dioxane, HOAc A novel intermediate compound in the preparation of the therapeutic compounds of the present invention is represented by formula VII

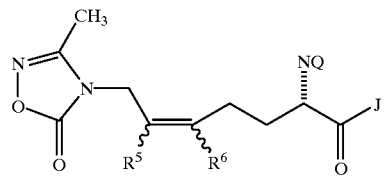

VII wherein $R^5$ is selected from the group consisting of H, F, and methyl;
$R^6$ is selected from the group consisting of H, F, and methyl;
with the proviso that either $R^5$ or $R^6$ must be F.

J is selected from the group consisting of hydroxy, alkoxy; and $NR^3R^4$ where $R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Q is H, or an appropriate nitrogen protecting moiety such as, for example, t-butoxycarbonyl, 2-(4-biphenylyl) propyl (2)oxycarbonyl (Bpoc), 2-nitro-phenylsulfenyl (Nps) or dithia-succionyl. Numerous protected amino groups useful in the present invention for are described by Theodora W. Greene and Peter G. M. Wuts (*Protective Groups in Organic Synthesis,* 3rd ed., John Wiley & Sons, New York, 1999, pp. 494–653). For example NZ can be a 4-chlorobenzylimino group. In one embodiment of the present invention, the protected amino group is any such group resulting from the reaction of an aldehyde with the corresponding amino group to form a Schiff base. A large variety of deprotecting reagents can be advantageously used in the present invention to effect the conversion of the intermediate to the desired compound. Many such deprotecting reagents are described by Greene and Wuts, supra. For example, when the protected amino group is a 4-chlorobenzylimino group or a t-butoxycarbonylamino group, preferably the deprotecting reagent is an acid. Some useful acid deprotecting agents include, without limitation, hydrochloric acid, hydrobromic acid, sulfuric acid, trifluoroacetic acid, phosphoric acid, phosphorus acid, and acetic acid.

The following examples are provided to illustrate the present invention and are not intended to limit the scope thereof. Those skilled in the art will readily understand that known variations of the conditions and processes of the following preparative procedures can be used to prepare these compounds.

EXAMPLE 1

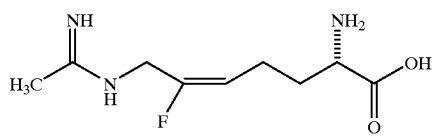

(2S,5E)-2-amino-6-fluoro-7-[(1-iminoethyl)amino]-5-heptenoic acid, dihydrochloride, monohydrate

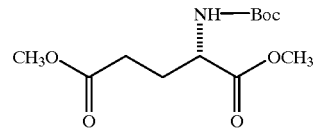

EX-1A)

Trimethylsilyl chloride (107.8 g, 1.00 mol) was added dropwise to a cooled solution of L-glutamic acid (30.00 g, 0.20 mol) in 300 mL of methanol at 0° C. The resulting clear, colorless solution was allowed to stir at room temperature. After 18 h, analysis by thin layer chromatography (30% ethyl acetate in hexane) showed that no starting material remained. The reaction was then cooled to 0° C., triethylamine (134 g, 1.33 mol) was added, and a white precipitate formed. Di-tert-butyldicarbonate (49 g, 0.23 mol) was added, and the mixture was allowed to warm to room temperature. After 3 h the solvent was removed, and 700 mL of diethyl ether was added. The solution was filtered, and the filter cake was rinsed with an additional 500 mL of diethyl ether. The filtrate was concentrated to 60.8 g (>95%) of a tan oil which was carried onto the next step without further purification. LCMS: m/z=298.1 [M+Na]$^+$. HRMS calcd. for $C_{12}H_{21}NO_6$: 276.1447 [M+H]$^+$, found: 276.1462. $^1$H NMR (CDCl$_3$) δ 1.45 (s, 9H), 1.95 (m, 1H), 2.50 (m, 1H), 2.40 (m, 2H), 3.69 (s, 3H), 3.75 (s, 3H), 4.32 (m, 1H), 5.15 (m, 1H).

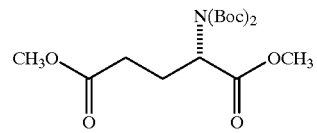

EX-1B)

To a solution of the crude product from EX-1A (60 g, 0.22 mol) in 300 mL of acetonitrile at room temperature was added 4-dimethylaminopyridine (5.3 g, 0.44 mol) and di-tert-butyldicarbonate (79.2 g, 0.36 mol). The resulting mixture was stirred for 2 days at room temperature, at which time analysis by thin layer chromatography (25% ethyl acetate in hexane) showed that most of the starting material was consumed. The solvent was removed in vacuo affording 85 g of a red oil. The crude material was purified by flash column chromatography on silica gel eluting with 1:10 ethyl acetate in hexane to give 66.4 g (81%) of the desired di-Boc product as a pale-yellow solid. LCMS: m/z=398.2 [M+Na]$^+$. HRMS calcd. for $C_{17}H_{29}NO_8$: 398.1791 [M+Na]$^+$, found: 398.1790. $^1$H NMR(CDCl$_3$) δ 1.48 (s, 18H), 2.19 (m, 1H), 2.41 (m, 2H), 2.46 (m, 1H), 3.66 (s, 3H), 3.70 (s, 3H), 4.91 (dd, 1H).

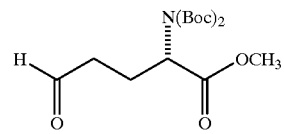

EX-1C)

A solution of DIBAL (64 mL of 1.0 M solution in hexanes, 63.9 mmol) was added dropwise to a cold solution of EX-1B (20 g, 53.3 mmol) in 400 mL of anhydrous diethyl ether at −78° C. over 30 min. After an additional 30 min at −78° C., the solution was quenched with water (12 mL, 666 mmol) and allowed to warm to room temperature. The cloudy mixture was diluted with 350 mL of ethyl acetate, dried over MgSO₄ and filtered through a pad of celite. The filtrate was concentrated to a yellow oil. The crude material, 18.9 g of yellow oil, was purified by flash column chromatography on silica gel eluting with 1:4 ethyl acetate in hexane to give 13.8 g (75%) of the desired aldehyde product as a clear oil. LCMS: m/z=368.2 [M+Na]⁺. ¹H NMR (CDCl₃) δ 1.48 (s, 18H), 2.19 (m, 1H), 2.41 (m, 2H), 2.46 (m, 1H), 3.70 (s, 3H), 4.91 (dd, 1H), 9.8 (s, 1H).

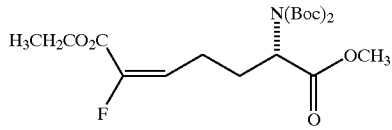

EX-1D)

To a cold (−78° C.) solution of triethyl 2-fluorophosphonoacetate (4.67 g, 19.3 mmol) in 20 mL of THF was added n-butyl lithium (10.9 mL of 1.6 M in hexane, 17.5 mmol). This mixture was stirred at −78° C. for 20 min producing a bright yellow solution. A solution of the product from EX-1C (6.0 g, 17.5 mmol) in 5 mL of THF was then added via syringe, and the resulting mixture was stirred for 2 h at −78° C., at which time analysis by thin layer chromatography (30% ethyl acetate in hexane) showed that no starting material remained. The reaction was quenched at −78° C. with sat. aqueous NH₄Cl (30 mL). The organic layer was collected, and the aqueous layer was extracted with diethyl ether (2×50 mL). The combined organics were washed with water (100 mL) and brine (100 mL), dried over MgSO₄, filtered and concentrated. The crude material, 8.6 g of a yellow oil, was purified by flash column chromatography on silica gel eluting with 1:4 ethyl acetate in hexane to give 6.05 g (79%) of the desired fluoro olefin product as a clear oil. ¹H NMR and ¹⁹F NMR indicated that the isolated product had an approximate E:Z ratio of 95:5. LCMS: m/z=456.2 [M+Na]⁺. HRMS calcd. for C₂₀H₃₂NO₈F: 456.2010 [M+Na]⁺, found: 456.2094. ¹H NMR (CDCl₃) δ 1.48 (s, 18H), 2.0 (m, 1H), 2.25 (m, 1H), 2.6 (m, 2H), 3.7 (s, 3H), 4.25 (m, 2H), 4.9 (m, 1H), 5.9 (dt, vinyl, 1H, J=20 Hz), 6.2 (dt, vinyl, 1H, J=30 Hz). ¹⁹F NMR (CDCl₃) δ −129.12 (d, 0.09F, J=31 Hz, 9% Z-isomer), −121.6 (d, 0.91F, J=20 Hz, 91% E-isomer).

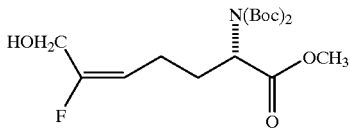

EX-1E)

To a solution of EX-1D (805 mg, 1.86 mmol) in 20 mL of methanol at room temperature was added solid NaBH₄ (844 mg, 22.3 mmol) in 200 mg portions. The reaction was stirred for 18 h at ambient temperature, at which time analysis by thin layer chromatography (30% ethyl acetate in hexane) showed that most of the starting material was consumed. The reaction was quenched with 20 mL of sat. aqueous NH₄Cl and extracted with ethyl acetate (2×35 mL). The organic layers were combined, dried over MgSO₄, filtered and concentrated. The crude material, 700 mg of clear oil, was purified by flash column chromatography on silica gel eluting with 1:4 ethyl acetate in hexane to give 353 mg (48%) of the desired allylic alcohol product as a clear oil, that contained primarily the desired E-isomer by ¹⁹F NMR. LCMS: m/z=414.2 [M+Na]⁺. ¹H NMR (CDCl₃) δ 1.48 (s, 18H), 1.95 (m, 1H), 2.1 (m, 1H), 2.2 (m, 1H), 2.35 (t, 1H), 3.7 (s, 3H), 4.25 (m, 2H), 4.8 (m, 1H), 5.15 (dt, 1H, J=20 Hz). ¹⁹F NMR (CDCl₃) δ −119.1 (d, 0.02F, J=37 Hz, 2% Z-isomer), −111.8 (d, 0.98F, J=24 Hz, 98% E-isomer).

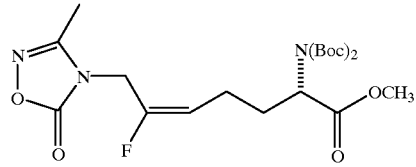

EX-1F)

To a mixture of EX-1E (1.37 g, 3.5 mmol), polymer-supported triphenylphosphine (3 mmol/g, 1.86 g, 5.6 mmol) and 3-methyl-1,2,4-oxadiazolin-5-one (450 mg, 4.55 mmol) in 50 mL of THF was added dropwise dimethylazodicarboxylate (820 mg, 5.6 mmol). The reaction was stirred for 1 h at room temperature, at which time analysis by thin layer chromatography (40% ethyl acetate in hexane) showed that no starting material remained. The mixture was filtered through celite, and the filtrate was concentrated. The resulting yellow oil was partitioned between 30 mL of methylene chloride and 30 mL of water. The organic layer was separated, washed with water (1×30 mL) and brine (1×30 mL), dried over MgSO₄, filtered and concentrated. The crude material, 1.8 g of a yellow oil, was purified by flash column chromatography on silica gel eluting with 1:4 ethyl acetate in hexane to give 670 mg (40%) of the desired protected E-allylic amidine product as a clear oil, that contained only the desired E-isomer by ¹⁹F NMR. LCMS: m/z=496.2 [M+Na]⁺. ¹H NMR (CDCl₃) δ 1.48 (s, 18H), 1.85 (m, 1H), 2.2 (m, 3H), 2.25 (s, 3H), 3.64 (s, 3H), 4.25 (m, 2H), 4.8 (m, 1H), 5.3 (dt, 1H, J=20 Hz). ¹⁹F NMR (CDCl₃) δ −110.8 (q, 1F, J=20 Hz).

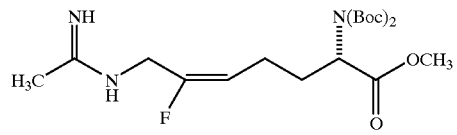

EX-1G)

The product from EX-1F (670 mg, 1.4 mmol) was dissolved in 25 mL of methanol and 25 mL of 25% acetic acid in water. Zinc dust (830 mg, 12.7 mmol) was added, and the mixture was agitated under sonication for 8 h, at which time HPLC analysis showed that only 20% of the starting material remained. The Zn dust was filtered from the reaction mixture, and the filtrate was stored at −20° C. for 12 h. The filtrate was warmed to room temperature, additional glacial acetic acid (7 mL) and zinc dust (400 mg, 6.1 mmol) were added, and the mixture was sonicated for 1 h at room temperature, at which time HPLC analysis showed 96% product. The mixture was filtered through celite, and the filtrate was concentrated. The crude material was purified by reverse-phase HPLC column chromatography on a YMC Combiprep column eluting over 8 min using a gradient of 20–95% A (A: 100% acetonitrile with 0.01% trifluoroacetic acid, B: 100% H₂O with 0.01% trifluoroacetic acid). Fractions containing product were combined and concentrated affording 344 mg (45%) of the desired acetamidine product as a trifluoroacetate salt, that contained only the desired E-isomer by ¹⁹F NMR. LCMS: m/z=432.3 [M+H]⁺. ¹H NMR (CD₃OD) δ 1.52 (s, 18H), 2.9 (m, 1H), 2.2 (m, 3H), 2.27 (s, 3H), 4.2 (d, 1H), 5.4 (dt, vinyl, 1H, J=20 Hz). ¹⁹FNMR(CD₃OD) δ −110.83 (m, 1F, J=20 Hz).

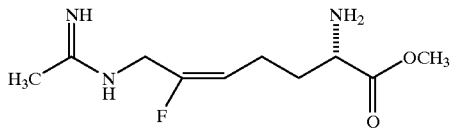

EX-1H)

A sample of the product of EX-1G is dissolved in glacial acetic acid. To this stirred solution is added 10 equivalents of 1N HCl in dioxane. After stirring this solution for ten minutes at room temperature, all solvent is removed in vacuo to generate the illustrated methyl ester dihydrochloride salt.

Example 1)

A solution of EX-1G (344 mg, 1.4 mmol) in 6 mL of 6.0 N HCl was refluxed for 1 h. The solvent was removed in vacuo. The resulting solid was dissolved in water and concentrated three additional times, followed by 5 subsequent times in 1.0 N HCl to remove any remaining TFA salts. Upon completion, 160 mg (37%) of the desired (2S,5E)-2-amino-6-fluoro-7-[(1-iminoethyl)amino]-5-heptenoic acid, dihydrochloride product was obtained as a white solid, m.p. 51.5–56.3° C., that contained only the desired E-isomer by ¹⁹F NMR. LCMS: m/z=218.1 [M+H]⁺. HRMS calcd. for C₉H₁₆FN₃O₂: 218.1305 [M+H]⁺, found: 218.1325. ¹H NMR (D₂O) δ 1.8 (m, 2H), 2.05 (m, 2H), 2.1 (s, 3H), 3.7 (t, 1H), 4.00 (d, 2H), 5.3 (dt, vinyl, 1H, J=21 Hz). ¹⁹F NMR (D₂O) δ −109.9 (m, 1F, J=20 Hz).

EXAMPLE 2

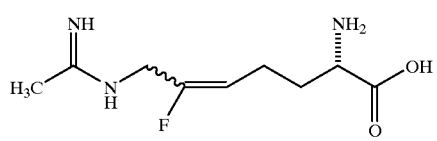

(2S,5E/Z)-2-amino-6-fluoro-7-[(1-iminoethyl) amino]-5-heptenoic acid, dihydrochloride

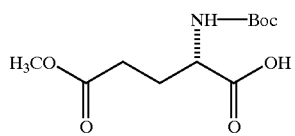

EX-2A)

To a cooled (0° C.) solution of L-glutamic acid 5-methyl ester (50.00 g, 0.31 mol) in 400 mL of 1:1 H₂O in dioxane was added triethylamine (38.35 g, 0.38 mol) followed by di-tert-butyldicarbonate (80.00 g, 0.37 mol). The resulting clear, colorless solution was allowed to stir at room temperature. After 18 h, analysis by thin layer chromatography (30% ethyl acetate in hexane) showed that no starting material remained. The reaction mixture was quenched with 200 mL of 1.0 N aqueous KHSO₄. The organic layer was removed, and the aqueous layer was extracted with ethyl acetate (3×100 mL). The organic layers were combined, dried over MgSO₄, filtered and concentrated to give 72.00 g (89%) of the desired product as a pale yellow oil. LCMS: m/z=284.1 [M+Na]⁺. ¹H NMR (CDCl₃) δ 1.50 (s, 9H), 2.00 (m, 1H), 2.20 (m, 1H), 2.42 (m, 2H), 3.66 (s, 3H), 4.34 (d, 1H), 5.24 (d, 1H).

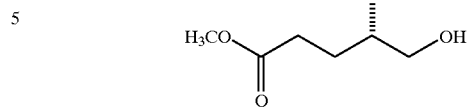

EX-2B)

To a solution of the product from EX-2A (72.60 g, 0.28 mol) in 300 mL of THF at −10° C. was quickly added 4-methylmorpholine (28.11 g, 0.28 mol) and isobutylchloroformate (37.95 g, 0.28 mol). The clear yellow solution immediately formed a white precipitate. After 4 min, the resulting cloudy yellow mixture was filtered, the filtrate was cooled to −10° C. and a solution of NaBH₄ (15.77 g, 0.42 mol) in 200 mL of H₂O was added dropwise while maintaining a subzero temperature. Once all of the NaBH₄ was added, the ice bath was removed, and the reaction was allowed to stir at room temperature for 1.5 h. The reaction mixture was quenched with 200 mL of H₂O. The organic layer was separated, and the aqueous layer was extracted with ethyl acetate (3×100 mL). The organic layers were combined, washed with brine, dried over MgSO₄, filtered and concentrated to give 58 g (85%) of the desired product as a yellow oil. LCMS: m/z=270.1 [M+Na]⁺. ¹H NMR (CDCl₃) δ 1.42 (s, 9H), 1.65 (m, 1H), 1.85 (m, 2H), 2.42 (t, 2H), 3.66 (s, 3H), 4.8 (d, 1H).

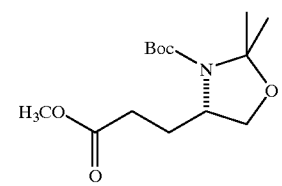

EX-2C)

To a solution of EX-2B (30.95 g, 0.13 mol) in 100 mL of benzene was added 2,2- dimethoxy propane (65.00 g, 0.63 mol) followed by p-toluenesulfonic acid (2.40 g, 12.5 mmol) and 5 g of 3 Å molecular sieves. The resulting mixture was refluxed for 2 h, at which time analysis by thin layer chromatography (30% ethyl acetate in hexane) showed complete reaction. The mixture was cooled to room temperature, diluted with diethyl ether (150 mL) and washed with sat. aqueous NaHCO₃ (100 mL) followed by brine (100 mL). The organic layer was dried over MgSO₄, filtered and concentrated. The crude material, 30.5 g of a yellow oil, was purified by flash column chromatography on silica gel eluting with 1:10 ethyl acetate in hexane to give 15.40 g (42%) of the desired product as a pale-yellow oil. LCMS: m/z=310.1 [M+Na]⁺. ¹H NMR (CDCl₃) δ 1.42 (s, 12H), 1.56 (d, 3H), 1.85 (m, 2H), 2.38 (m, 2H), 3.66 (s, 3H), 3.7 (d, 1H), 3.95 (m, 2H).

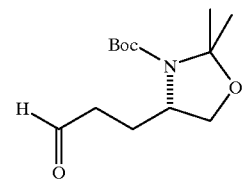

EX-2D)

DIBAL (6.0 mL of 1.0 M solution in toluene) was added dropwise to a cold (−78° C.) solution of the product from EX-2C (1.00 g, 3.00 mmol) in 10 mL of methylene chloride. After 30 min, the reaction was quenched with 5 mL sat. potassium sodium tartrate (Rochelle salt), then allowed to warm to room temperature. The mixture was then filtered through a pad of celite, dried over MgSO$_4$, re-filtered and concentrated to give a yellow oil. The crude material, 610 mg of a yellow oil, was purified by flash column chromatography on silica gel eluting with 1:4 ethyl acetate in hexane to give 550 mg (71%) of the desired product as a clear oil. $^1$H NMR (CDCl$_3$) δ 1.50 (s, 12H), 1.58 (d, 3H), 2.00 (m, 2H), 2.5 (m, 2H), 3.7 (d, 1H), 3.95 (m, 2H), 9.8 (s, 1H).

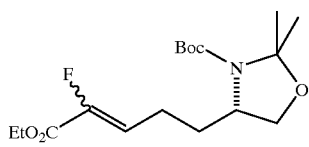

EX-2E)

To an ice cold (0° C.) solution of triethyl 2-fluorophosphonoacetate (6.70 g, 27.6 mmol) in 100 mL of methylene chloride was added 1,8-diazabicyclo[5.4.0]undec-7-ene (4.70 g, 31.0 mmol). The mixture was stirred at 0° C. for 1 h resulting in an orange solution. Then, a ice cold (0° C.) solution of the product from EX-2D (5.71 g, 22.2 mmol) in 15 mL of methylene chloride was added via syringe, and the resulting mixture was stirred for 18 h at ambient temperature, at which time analysis by thin layer chromatography (30% ethyl acetate in hexane) showed that no starting material remained. The solvent was removed in vacuo, and the resulting mixture was partitioned between 200 mL of ethyl acetate and 100 mL of water. The organic layer was collected, and the aqueous layer was extracted with ethyl acetate (2×50 mL). The combined organic layers were washed with 1.0 M aqueous KHSO$_4$ (100 mL), water (100 mL) and brine (100 mL), dried over MgSO$_4$, filtered and concentrated to give the desired fluoro olefin product as a yellow oil (8.0 g). $^1$H NMR and $^{19}$F NMR indicated that the isolated product had an approximate Z:E ratio of 70:30. LCMS: m/z=368.2 [M+Na]$^+$. $^1$H NMR (CDCl$_3$) δ 5.9–6.0 (dt, 1H, J=20 Hz), 6.05–6.20 (dt, 1H, J=33 Hz). $^{19}$F NMR (CDCl$_3$) δ −129.89 (d, 0.7F, J=38 Hz, 70% Z-isomer), −122.05 (d, 0.3F, J=20 Hz, 30% E-isomer). This mixture was carried on crude without further purification.

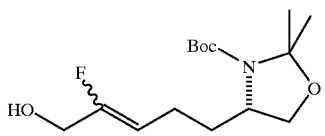

EX-2F)

To an ice cold (0° C.) solution of the product from EX-2E (8.0 g, 23.0 mmol) in 70 mL of THF was added LiBH$_4$ (12.7 mL of 2.0 M in THF, 25.0 mmol) via syringe. The reaction mixture was stirred for 18 h at ambient temperature at which time analysis by thin layer chromatography (30% ethyl acetate in hexane) showed that no starting material remained. The THF was removed, and the resulting mixture was dissolved in methylene chloride. After cooling to 0° C., 1.0 M aqueous KHSO$_4$ was slowly added to quench the reaction. The mixture was then extracted with ethyl acetate (3×50 mL). The organic layers were combined, dried over MgSO$_4$, filtered and concentrated. The crude material, 8.0 g of a clear oil, was purified by flash column chromatography on silica gel eluting with 1:4 ethyl acetate in hexane to give 900 mg (13%) of the desired product as a clear oil. LCMS: m/z=326.2 [M+Na]$^+$. $^1$H NMR (CDCl$_3$) δ 4.79–4.94 (dm, 1H), 5.10–5.25 (dt, 1H). $^{19}$F NMR (CDCl$_3$) δ —119.82 (dt, 0.7F, J=38 Hz, 70% Z-isomer), −111.09 (dt, 0.3F, J=27 Hz, 30% E-isomer).

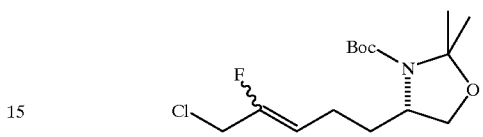

EX-2G)

To an ice cold (0° C.) solution of the product from EX-2F (950 mg, 3.1 mmol) in 5 mL of pyridine was added methanesulfonyl chloride (390 mg, 3.4 mmol). The reaction was stirred for 5 min at 0° C., then warmed to room temperature and stirred for 3 h, at which time analysis by thin layer chromatography (30% ethyl acetate in hexane) showed that no starting material remained. The reaction was diluted with diethyl ether (10 mL) and washed with sat. aqueous NaHCO$_3$ (20 mL) followed by 1.0 M citric acid (20 mL). The organic layer was dried over MgSO$_4$, filtered and concentrated to give 500 mg (51%) of the desired allylic chloride product as a white solid. This product was carried forward without further purification. LCMS: m/z=344.1 [M+Na]$^+$.

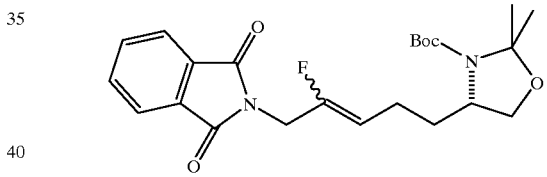

EX-2H)

To a stirring solution of the product from EX-2G (440 mg, 1.37 mmol) in 10 mL of DMF was added potassium phthalimide (290 mg, 1.57 mmol). The resulting mixture was heated under reflux for 18 h, at which time analysis by thin layer chromatography (30% ethyl acetate in hexane) showed that no starting material remained. The cooled mixture was diluted with 30 mL of water, extracted twice with ethyl acetate (30 mL), dried over MgSO$_4$, filtered and concentrated to give 540 mg (91%) of the desired product as a yellow oil. LCMS: m/z=455.2 [M+Na]$^+$. HRMS calcd. for: 433.2139 [M+H]$^+$, found: 433.2144. $^1$H NMR (CDCl$_3$) δ 1.4 (s, 18H), 1.6 (m, 6H), 2.05 (m, 2H), 3.6–4.42 (m, 4H), 4.9 (dt, vinyl, 1H), 5.2, (m, vinyl, 1H), 7.7 (m, 2H), 7.9 (m, 2H). $^{19}$F NMR (CDCl$_3$) δ −117.09 (m, 0.7F, J=38 Hz, 70% Z-isomer), −111.61 (m, 0.3F, J=22 Hz, 30% E-isomer).

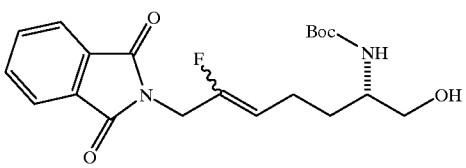

EX-2I)

The product from EX-2H (600 mg, 1.38 mmol) was dissolved in 8 mL of acetic acid and 2 mL of water. The mixture was stirred at room temperature overnight at which time analysis by thin layer chromatography (30% ethyl acetate in hexane) showed that no starting material remained. The solution was concentrated under a stream of nitrogen, and the crude product was purified by flash column chromatography on silica gel eluting with 1:2 ethyl acetate in hexane to give 248 mg (63%) of the desired product as a white solid. LCMS: m/z=415.1 [M+Na]$^+$. $^1$H NMR (CDCl$_3$) δ 1.41 (s, 9H), 1.56 (m, 2H), 2.15 (m, 1H), 3.64 (m, 2H), 4.35 (d, 2H), 4.9 (dt, vinyl, 1H, J=37 Hz), 7.73 (m, 2H), 7.86 (m, 2H). $^{19}$F NMR (CDCl$_3$) δ −116.96 (dt, 0.8F, J=37 Hz, 80% Z-isomer), −111.09 (dt, 0.2F, J=22 Hz, 20% E-isomer).

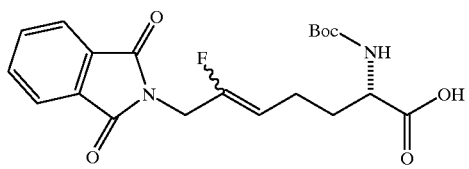

EX-2J)

To a stirring solution of the product from EX-2I (237 mg, 0.605 mmol) in 6 mL of DMF was added pyridinium dichromate (1.14 g, 3.03 mmol). The solution turned dark orange and was allowed to stir at room temperature for 18 H, at which time it was poured into 20 mL of H$_2$O. The mixture was extracted with ethyl acetate (4×25 mL). The combined organic layers were washed with 5% aqueous KHCO$_3$ (3×25 mL). The aqueous layer was acidified with 1.0 M KHSO$_4$ to pH=3 followed by extraction with ethyl acetate (3×50 mL). The combined organic layers were concentrated to yield 235 mg (95%) of the desired amino acid product. The resulting white solid was carried on crude without further purification. LCMS: m/z 429.1 [M+Na]$^+$.

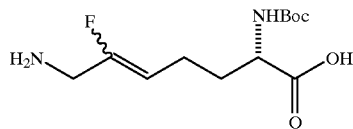

EX-2K)

To stirring solution of the product from EX-2J (230 mg, 0.56 mmol) in 7 mL of ethanol was added hydrazine hydrate (70 mg, 1.13 mmol), and the resulting solution was refluxed for 2 h forming a white precipitate. The solvent was removed in vacuo. The resulting white solid was dissolved in 8 mL of water and acidified to pH=4 with glacial acetic acid. It was then cooled in an ice bath and filtered. The filtrate was concentrated to give 136 mg (87%) of the desired allyl amine product as yellow crystals which were carried onto the next step without purification. LCMS: m/z=277.1 [M+H]$^+$.

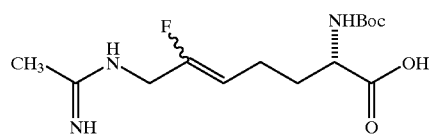

EX-2L)

To a stirring solution of the product from EX-2K (136 mg, 0.50 mmol) in 6 mL of DMF was added ethyl acetimidate (252 mg, 2.04 mmol) in 3 portions over 1.5 h intervals. After the addition was complete, the mixture was stirred overnight at room temperature. The pink solution was filtered, and the filter cake was washed with water. The solvent was removed in vacuo, and the resulting yellow oil was purified by reverse-phase HPLC using a YMC Combiprep ODS-A semi-prep column eluting with a 7 minute gradient of 1–50% A (A: 100 acetonitrile with 0.05% TFA, B: 100 water with 0.05% TFA). Fractions containing product were combined and concentrated to afford approximately 50 mg of the desired acetamidine product as a trifluoroacetate salt which was carried onto the next step. LCMS: m/z=318.2 [M+H]$^+$.

Example 2)

The product from EX-2L was dissolved in 6 mL of 6.0 N HCl and stirred for 1 h at room temperature. The solvent was removed in vacuo. The resulting solid was dissolved in water and concentrated three additional times to remove TFA salts. When $^{19}$F NMR indicated that all of the TFA was removed, the product was dried in vacuo to give 30 mg (20%, combined yield over two steps) of a 20:80 E:Z mixture containing the desired (2S,5E)-2-amino-6-fluoro-7-[(1-iminoethyl)amino]-5-heptenoic acid, dihydrochloride and (2S,5Z)-2-amino-6-fluoro-7-[(1-iminoethyl)amino]-5-heptenoic acid, dihydrochloride as a foamy clear solid. HRMS calcd. for C$_9$H$_{16}$FN$_3$O$_2$: 218.1305 [M+H]$^+$, found: 218.1309. $^1$H NMR (D$_2$O) δ 2.01 (m, 2H), 2.21 (s, 3H), 2.24 (m, 2H), 3.96 (t, 1H), 4.00 (d, 2H), 5.07 (dt, vinyl, 1H, J=37 Hz), 5.4 (dt, vinyl, 1H, J=37 Hz). $^{19}$F NMR (D$_2$O) δ −116.8 (m, 0.8F, J=37 Hz, 80% Z-isomer), −109.6 (m, 0.2F, J=21 Hz, 20% E-isomer).

EXAMPLE 3

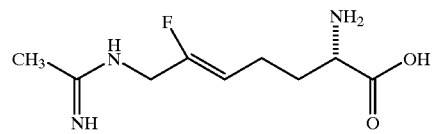

(2S,5Z)-2-amino-6-fluoro-7-[(1-iminoethyl)amino]-5-heptenoic acid, dihydrochloride

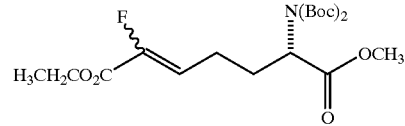

EX-3A)

Triethyl 2-fluoro-phosphonoacetate (3.54 g, 14.6 mmol) was dissolved in 20 mL of CH$_2$Cl$_2$ at 0° C., and 1,8-diazabicyclo[5.4.0]undec-7-ene (2.4 mL, 16.4 mmol) was added. The mixture was stirred at 0° C. for 20 min producing an orange solution. A solution of the aldehyde product from EX-1C (4.04 g, 11.7 mmol) was then added at 0° C., and the resulting brown mixture was stirred overnight at room temperature, at which time LCMS indicated that no starting material remained. The solvent was removed, and the residue was partitioned between water (60 mL) and ethyl acetate (120 mL). The organic layer was collected, and the aqueous layer was extracted with ethyl acetate (2×50 mL). The combined organic layers were washed with water (60 mL) and 10% aqueous KHSO$_4$ (60 mL), dried over MgSO$_4$, filtered and concentrated. The crude material, 5.7 g of an orange oil, was purified by flash column chromatography on silica gel eluting with 10% ethyl acetate in hexane to give 3.5 g (69%) of the desired fluoro olefin product as a clear oil. $^1$H NMR and $^{19}$F NMR indicated that the isolated product had an Z/E ratio of 70:30. HRMS calcd. for $C_{20}H_{32}O_8FN$: 456.2010 [M+Na]$^+$, found 456.2017. $^1$H NMR (CDCl$_3$) δ 1.48 (s, 18H), 2.0 (m, 1H), 2.25 (m, 1H), 2.6 (m, 2H), 3.7 (s, 3H), 4.25 (m, 2H), 4.9 (m, 1H), 5.9 (dt, vinyl, 1H, J=21.2 Hz), 6.1 (dt, vinyl, 1H, J=32.4 Hz). $^{19}$F NMR (CDCl$_3$) δ: –129.4 (d, 0.7F, J=34 Hz, 70% Z isomer), –121.6 (d, 0.3F, J=22 Hz, 30% E isomer).

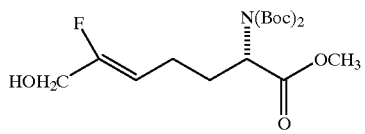

EX-3B)

The ester product from EX-3A (3.5 g, 8.1 mmol) was dissolved in 80 mL of methanol at room temperature, solid NaBH$_4$ (3 g, 80 mmol) was then added in portions. The mixture was stirred at room temperature for 18 h, at which time HPLC analysis indicated that the reaction was >90% complete. The reaction was quenched with sat NH$_4$Cl. The product was extracted with ethyl acetate and dried over Na$_2$SO$_4$. The organic layer was evaporated to give 3.2 g of crude product as a colorless oil, which was purified by Biotage flash column chromatography eluting with 20%–30% ethyl acetate in hexane to give 2.11 g (67%) of a Z/E mixture of the fluoro olefin product as a clear oil along with 0.41 g (13%) of the desired pure (Z:E=97:3 by $^{19}$F NMR) Z-isomer product as a clear oil. HRMS calcd. for $C_{18}H_{30}NO_7F$: 414.1904 [M+Na]$^+$, found 414.1911. $^1$H NMR (CDCl$_3$) δ 1.48 (s, 18H), 2.0 (m, 1H), 2.2 (m, 3H), 3.7 (s, 3H), 4.1 (dd, 2H, J=17 Hz), 4.8 (dt, 1H, J=39 Hz), 4.9 (m, 1H). $^{19}$F NMR (CDCl$_3$) δ –119.1 (dt, 1F, J=39 Hz, J=17 Hz).

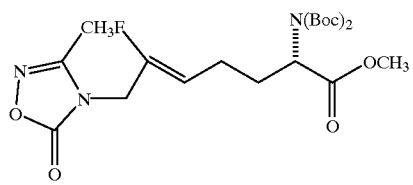

EX-3C)

The Z-alcohol product from EX-3B (390 mg, 1 mmol) and 3-methyl-1,2,4-oxadiazolin-5-one (130 mg, 1.3 mmol) were dissolved in 20 mL of THF. Then polymer supported-PPh$_3$ was added into the solution, and the mixture was gently stirred for 10 min. Then diethyl azodicarboxylate was added dropwise, and the mixture was stirred for 1 h at room temperature, at which time LCMS analysis indicated product formation and that no starting material was present.

The polymer was filtered off through a celite pad, and the pad was washed with THF. The filtrate was evaporated to give 1.0 g of crude product which was purified by Biotage flash column chromatography eluting with 20% to 30% ethyl acetate in hexane to give 500 mg of product, contaminated with some hydrazide by-product. This material was further purified by Biotage flash column chromatography eluting with 98:2:0.01 of methylene chloride:methanol:ammon-ium hydroxide to give 180 mg (38%) of the desired protected amidine product as a clear oil, that contained only the desired Z-isomer by $^{19}$F NMR.

HRMS calcd. for $C_{21}H_{32}N_3O_8F$: 491.2517 [M+NH$_4$]$^+$, found 491.2523. $^1$H NMR (CDCl$_3$) δ 1.5 (s, 18H), 1.9 (m, 1H), 2.1 (m, 3H), 2.3 (s, 3H), 3.7 (s, 3H), 4.2 (d, 2H), 4.8 (m, 1H), 5.0 (dt, 1H, J=36 Hz). $^9$F NMR (CDCl$_3$) δ –116.5 (dt, 1F, J=38 Hz).

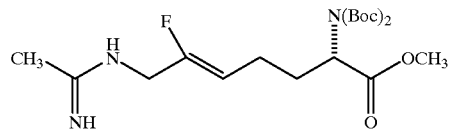

EX-3D)

The product from EX-3C (88 mg, 0.19 mmol) was dissolved in 4 mL of 25% acetic acid in water containing a few drops of methanol, and then Zn dust (109 mg, 1.67 mmol) was added. The mixture was agitated under sonication for 3 h. The Zn was filtered off through a celite pad, and the pad was washed with water. The filtrate was evaporated to dryness to give crude product which was purified by reverse-phase HPLC column chromatography on a YMC Combiprep column eluting over 8 min with a gradient of 20–80% A (A: 100% ACN with 0.01% TFA, B: 100% H$_2$O with 0.01% TFA). The desired product was collected in two fractions, and the combined fractions were concentrated. The product was obtained as a colorless oil as a mixture of trifluoroacetate salts that contained only the desired Z-isomer by $^{19}$F NMR: 30% was mono Boc-protected product: HRMS calcd. for $C_{15}H_{26}N_3O_4F$: 332.1986 [M+H]$^+$, found 332.2001, and 70% was di-Boc-protected product: HRMS calcd. for $C_{20}H_{34}N_3O_6F$: 432.2510 [M+H]$^+$, found 432.2503. $^1$H NMR of the di-Boc product (D$_2$O) δ 1.3 (s, 18H), 1.8 (m, 1H), 2.1 (m, 3H), 2.1 (s, 3H), 3.6 (s, 3H), 3.9 (d, 2H), 4.9 (dt, vinyl, 1H, J=37 Hz). $^{19}$F NMR (D$_2$O) δ –117.3 (dt, 1F, J=37 Hz).

Example 3)

The combined mono- and di-BOC products from EX-3D were dissolved in 30 mL of 6N HCl, and the solution was refluxed for 4 h, at which time LCMS analysis indicated complete reaction. The excess HCl and water was removed in vacuo. Upon completion, 9 mg (40% combined yield for two steps) of the desired (2S,5Z)-2-amino-6-fluoro-7-[(1-iminoethyl)amino]-5-heptenoic acid, dihydrochloride product was obtained as a light yellow, very hygroscopic foam, that contained only the desired Z-isomer by $^{19}$F NMR. HRMS calcd. for $C_9H_{16}N_3O_2F$: 218.1305 [M+H]$^+$, found 218.1320. $^1$H NMR (D$_2$O) δ 1.3 (s, 18H), 1.9 (m, 2H), 2.1 (m, 2H), 2.1 (s, 3H), 3.8 (t, 1H), 3.9 (d, 2H), 4.9 (dt, vinyl, 1H, J=37 Hz). $^{19}$F NMR (D$_2$O) 67 –117.3 (dt, 1F, J=37 Hz).

EXAMPLE 4

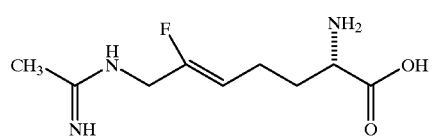

(2S,5Z)-2-amino-6-fluoro-7-[(1-iminoethyl)amino]-5-heptenoic acid, trihydrochloride, dihydrate

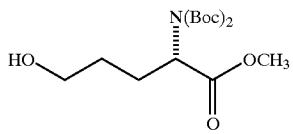

EX-4A)

The product from EX-1B (3.75 g, 10 mmol) was dissolved in 60 mL of methanol, and solid NaBH$_4$ (4 g, 106 mmol) was added in portions at room temperature over 10 h, at which time HPLC analysis indicated approximately 84% reduction. The reaction mixture was quenched with sat. NH$_4$Cl, and was then extracted with ethyl acetate three times. The combined organic layers were dried over MgSO$_4$, filtered, and evaporated to give 3.2 g of crude product as a yellow oil. HRMS calcd. for C$_{16}$H$_{29}$NO$_7$: 348.2022 [M+H]$^+$, found: 348.2034. $^1$H NMR (CD$_3$OD) δ 4.9 (q, 1H), 3.7 (s, 3H), 3.5 (t, 2H), 3.2 (m, 1H), 2.1 (m, 1H), 1.9 (m, 2H), 1.5 (s, 18H).

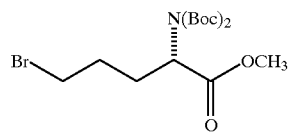

EX-4B)

The alcohol product from EX-4A (3.2 g, 9.0 mmol) was dissolved in 100 mL of THF and cooled in an ice bath. Carbon tetrabromide (4.27 g, 12.9 mmol) was added, and the resulting solution was stirred at 0° C. for 30 min under nitrogen. Polymer-supported PPh$_3$ was added, and the mixture was gently stirred at 0° C. for 1 h and then overnight at room temperature. The polymer was removed by filtration through celite, and the celite pad was washed with THF. The filtrate was evaporated to give crude product, which was purified by Biotage flash column chromatography eluting with 1:3 ethyl acetate in hexane to give 2.0 g (54%, combined yield over 2 steps) of the desired bromo product as a colorless oil. HRMS calcd. for C$_{16}$H$_{28}$NO$_6$Br: 410.1178 [M+H]$^+$, found: 410.1137. $^1$H NMR (CDCl$_3$) δ 4.9 (q, 1H), 3.7 (s, 3H), 3.4 (m, 2H), 2.2 (m, 2H), 1.9 (m, 2H), 1.5 (s, 18H).

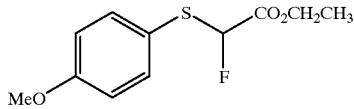

EX-4C)

A solution of NaOEt (21% in EtOH, 41.1 mL, 0.11 mol) in 60 mL of ethanol was treated with p-methoxy benzenethiol (14.0 g, 0.1 mol), followed by ethyl chlorofluoroacetate (18.3 g, 0.13 mol). The mixture was stirred at room temperature for 2 h and diluted with 250 mL of 1:1 hexane in ethyl acetate. The organic layer was washed with water three times, and dried over Na$_2$SO$_4$. The dried organic layer was evaporated to give 25 g of crude product which was carried forward without further purification. LCMS for C$_{11}$H$_{13}$O$_3$SF: m/z =267.10 [M+Na]$^+$. $^1$H NMR (CDCl$_3$) δ 7.5 (d, 2H), 6.9 (d, 2H), 6.0 (d, 1H, J=51.9 Hz), 4.2 (q, 2H), 3.8 (s, 3H), 1.2 (t, 3H). $^{19}$F NMR (CDCl$_3$) δ −146.2 (d, 1F, J=53.6 Hz).

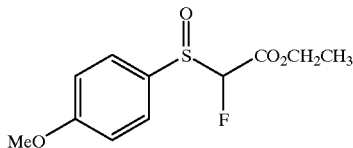

EX-4D)

A solution of the crude product from EX-4C (24 g, 0.1 mol) in 200 mL of methylene chloride was cooled to −78° C. and treated with 3-chloroperbenzoic acid (27 g, 0.12 mol) in 200 mL of methylene chloride. The reaction mixture was slowly warmed to room temperature and stirred overnight, at which time LCMS analysis indicated product formation and that no starting material remained. The solid was filtered off, and the filtrate was washed with sat. NaHCO$_3$ and NH$_4$Cl. The organic layer was dried over MgSO$_4$ and evaporated to give 30 g of an orange oil, which was purified by Biotage flash column chromatography eluting with 2:1 hexane in ethyl acetate to give 17.5 g (70%) of the desired sulfoxide product as an off-white oil. HRMS calcd. for C$_{11}$H$_{13}$O$_4$FS: 261.0597 [M+H]$^+$, found: 261.0598. $^1$H NMR (CDCl$_3$) δ 7.6 (m, 2H), 7.0 (m, 2H), 5.6 (d, 1H, J=50 Hz major diastereomer), 5.4 (d, 1H, J=49 Hz minor diastereomer), 4.2 (q, 2H), 3.8 (s, 3H), 1.2 (t, 3H). $^{19}$F NMR (CDCl$_3$) δ −194.3 (d, 1F, J=53.6 Hz major diastereomer), −191.7 (d, 1F, J=50.4 Hz minor diastereomer).

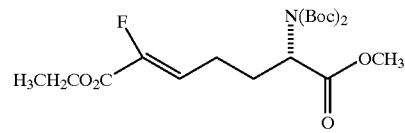

EX-4E)

A suspension of NaH (60% in mineral oil, 212 mg, 5.3 mmol) in 6 mL of dried DMF was cooled to 0° C. under nitrogen and treated with a solution of the sulfoxide product from EX-4D (1.25 g, 4.8 mmol) in 2 mL of DMF. After stirring at room temperature for 20 min, the mixture was cooled to 5° C., and the bromo procduct from EX-4B (2.17 g, 5.3 mmol) was added in one portion. The reaction was stirred at room temperature for 3 h, then heated at reflux at 95° C. for 1 h, at which time LCMS analysis indicated product formation. The mixture was poured into an ice/aqueous NH$_4$Cl mixture. The product was extracted with 1:1 hexane in ethyl acetate.

The organic layer was dried over Na$_2$SO$_4$ and evaporated to give 3.17 g of a crude yellow oil, which was purified by Biotage flash column chromatography eluting with 10% ethyl acetate in hexane to give 1.05 g (50%) of the desired fluoro olefin ester product as a colorless oil. $^{19}$F NMR indicated that the isolated product contained 95:5 the desired Z-isomer. HRMS calcd. for C$_{20}$H$_{32}$O$_8$FN: 456.2010 [M+Na]$^+$, found: 456.2017. $^1$H NMR (CDCl$_3$) δ 1.5 (s, 18H), 2.0 (m, 1H), 2.3 (m, 4H), 3.7 (s, 3H), 4.3 (m, 2H), 4.9 (m, 1H), 6.1 (dt, vinyl, 1H, J=32.4 Hz, Z isomer). $^{19}$F NMR (CDCl$_3$) δ −129.4 (d, 0.95F, J=34.8 Hz, 95% Z isomer), −121.6 (d, 0.05F, J=21.6 Hz, 5% E isomer).

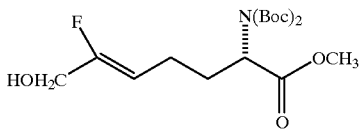

EX-4F)

The ester product from EX-4E (1.05 g, 2.4 mmol) was dissolved in methanol at room temperature, and solid NaBH$_4$ was added in portions. The mixture was stirred at room temperature for 18 h, then 2 mL of water was added, and the mixture was stirred for an additional 3 h, at which time HPLC analysis indicated the reaction was >95% complete. The reaction was quenched with sat NH$_4$Cl. The product was extracted with ethyl acetate, and the organic layer was dried over Na$_2$SO$_4$ and evaporated to give 0.95 g of crude product as colorless oil. $^{19}$F NMR indicated that the isolated crude product contained only the desired Z-isomer. HRMS calcd. for C$_{18}$H$_{30}$NO$_7$F: 414.1904 [M+Na]$^+$, found: 414.1949. $^1$H NMR (CDCl$_3$) δ 1.48 (s, 18H), 2.0 (m, 1H), 2.2 (m, 3H), 3.7 (s, 3H), 4.1 (dd, 2H, J=17 Hz), 4.8 (dt, 1H, J=36 Hz), 4.9 (m, 1H). $^{19}$F NMR (CDCl$_3$) δ −119.1 (dt, 1F, J=38 Hz, J=17 Hz).

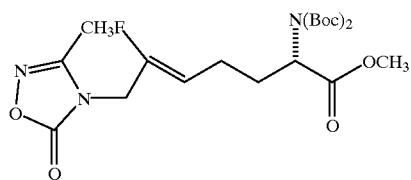

EX-4G)

The alcohol product from EX-4F (0.95 g, 2.4 mmol) and 3-methyl-1,2,4-oxadiazolin-5-one (290 mg, 2.9 mmol) were dissolved in 60 mL of THF. Polymer-bound triphenyl phosphine was added, and the mixture was gently stirred for 10 min. Then dimethyl azodicarboxylate was added dropwise, and the mixture was stirred for 1 h at room temperature, at which time LCMS analysis indicated product formation and that no starting material remained. The polymer was filtered off through a celite pad, and the pad was washed with THF. The filtrate was evaporated to give a residue which was partitioned between methylene chloride and water. The organic layer was washed with water twice, dried over MgSO$_4$, and evaporated to give 1.3 g of crude product which was purified by Biotage flash column chromatography eluting with 20% to 30% ethyl acetate in hexane to give 390 mg (34%, combined yield over 2 steps) of the desired protected amidine product as a colorless oil. $^{19}$F NMR indicated that the isolated product contained only the desired Z-isomer. HRMS calcd. for C$_{21}$H$_{32}$N$_3$O$_8$F: 491.2517 [M+NH$_4$]$^+$, found: 491.2523. $^1$H NMR (CDCl$_3$) δ 1.5 (s, 18H), 1.9 (m, 1H), 2.1 (m, 3H), 2.3 (s, 3H), 3.7 (s, 3H), 4.2 (d, 2H), 4.8 (m, 1H), 5.0 (dt, 1H, J=36 Hz). $^{19}$F NMR (CDCl$_3$) δ −116.5 (dt, 1F, J=38 Hz).

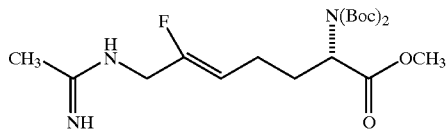

EX-4H)

The product from EX-4G (390 mg, 0.82 mmol) was dissolved in 20 mL of 25% HOAc in water containing 4 mL of methanol, and Zn dust (482 mg, 7.42 mmol) was added in two portions. The mixture was agitated under sonication for 3 h. The Zn was filtered off through a celite pad, and the pad was washed with water. The filtrate was evaporated to dryness to give crude product which was purified by reverse-phase-HPLC. Fractions containing the desired products were collected, combined and concentrated. The products were obtained as colorless oils as a mixture of trifluoroacetate salts, that contained only the desired Z-isomer by $^{19}$F NMR: 30% was mono-Boc protected product: HRMS calcd. for C$_{15}$H$_{26}$N$_3$O$_4$F: 332.1986 [M+H]$^+$, found 332.2001; 70% was diBoc protected product: HRMS calcd. for C$_{20}$H$_{34}$N$_3$O$_6$F: 432.2510 [M+H]$^+$, 432.2503. $^1$H NMR of diBoc product (D$_2$O) δ 1.3 (s, 18H), 1.8 (m, 1H), 2.1 (m, 3H), 2.1 (s, 3H), 3.6 (s, 3H), 3.9 (d, 2H), 4.9 (dt, vinyl, 1H, J=37 Hz). $^{19}$F NMR (D$_2$O) δ −117.3 (dt, 1F, J=37 Hz).

Example 4)

The mono and diBOC products from EX-4H were dissolved in 80 mL of 6N HCl and the solution was heated at reflux for 1 hour, at which time LCMS analysis indicated complete reaction. The excess HCl and water was removed in vacuo to give 150 mg (50% combined yield over 2 steps) of the desired (2S,5Z)-2-amino-6-fluoro-7-[(1-iminoethyl)amino]-5-heptenoic acid, trihydrochloride, dihydrate product as a light yellow very hygroscopic foam. HRMS calcd. for C$_9$H$_{16}$N$_3$O$_2$F: 218.1305 [M+H]$^+$, found 218.1290. $^1$H NMR (D$_2$O) δ 1.3 (s, 18H), 1.9 (m, 2H), 2.1 (m, 2H), 2.1 (s, 3H), 3.8 (t, 1H), 3.9 (d, 2H), 4.9 (dt, vinyl, 1H, J=37 Hz). $^{19}$F NMR (D$_2$O) δ −117.3 (dt, 1F, J=37 Hz). Anal. Calcd. for C$_9$H$_{16}$N$_3$O$_2$F.3HCl.2H$_2$O: C, 29.81; H, 6.39; N, 11.59; found C, 29.80; H, 6.11; N, 11.20.

EXAMPLE 5

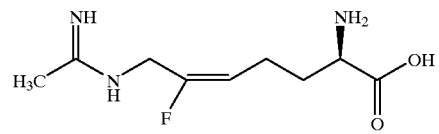

(2R,5E)-2-amino-6-fluoro-7-[(1-iminoethyl)amino]-5-heptenoic acid, dihydrochloride, monohydrate

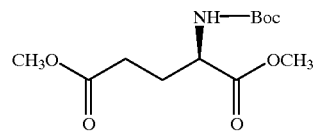

EX-5A)

Trimethylsilyl chloride is added dropwise to a cooled solution of D-glutamic acid in methanol at 0° C. The resulting clear, colorless solution is allowed to stir at room temperature until analysis by thin layer chromatography shows that no starting material remains. The reaction is then cooled to 0° C., triethylamine is added, and a white precipitate forms. Di-tert-butyldicarbonate is added, and the mixture is allowed to warm to room temperature. After 3 h the solvent is removed, and diethyl ether is added. The solution is filtered, and the filter cake is rinsed with additional diethyl ether. The filtrate is concentrated to give the desired mono-Boc diester product which is carried onto the next step without further purification.

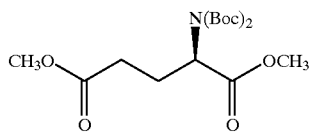

EX-5B)

To a solution of the crude product from EX-5A in acetonitrile at room temperature is added 4-dimethylaminopyridine and di-tert-butyldicarbonate. The resulting mixture is stirred at room temperature, until analysis by thin layer chromatography shows that most of the starting material is consumed. The solvent is removed in vacuo, and the resulting residue is purified by flash column chromatography on silica gel to give the desired di-Boc protected diester product.

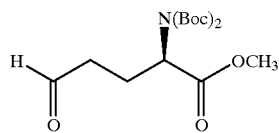

EX-5C)

A solution of DIBAL is added dropwise to a cold solution of EX-5B in anhydrous diethyl ether at −78° C. After 30 min at −78° C., the solution is quenched with water and allowed to warm to room temperature. The resulting cloudy mixture is diluted with ethyl acetate, dried over MgSO$_4$ and filtered through a pad of celite. The filtrate is concentrated, and the resulting residue is purified by flash column chromatography on silica gel to give the desired aldehyde product

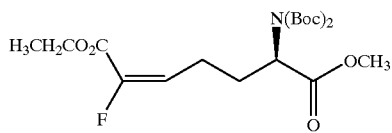

EX-5D)

To a cold (−78° C.) solution of triethyl 2-fluorophosphonoacetate in THF is added n-butyl lithium. This mixture is stirred at −78° C. producing a bright yellow solution. A solution of the product from EX-5C in THF is then added via syringe, and the resulting mixture is stirred at −78° C., until analysis by thin layer chromatography shows that no starting material remains. The reaction is quenched at −78° C. with sat. aqueous NH$_4$Cl. The organic layer is collected, and the aqueous layer is extracted with diethyl ether. The combined organics are washed with water and brine, dried over MgSO$_4$, filtered and concentrated. The crude material is then purified by flash column chromatography on silica gel to give the desired fluoro olefin product.

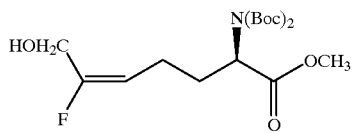

EX-5E)

To a solution of EX-5D in methanol at room temperature is added solid NaBH$_4$ in portions. The reaction is stirred at ambient temperature until analysis by thin layer chromatography shows that most of the starting material is consumed. The reaction is quenched with sat. aqueous NH$_4$Cl and extracted with ethyl acetate. The organic layers are combined, dried over MgSO$_4$, filtered and concentrated. The crude material is purified by flash column chromatography on silica gel to give the desired allylic alcohol product.

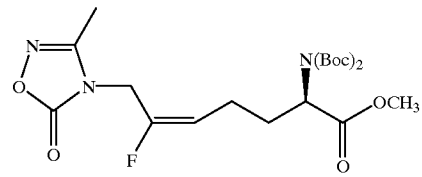

EX-5F)

To a mixture of EX-5E, polymer-supported triphenylphosphine and 3-methyl-1,2,4-oxadiazolin-5-one in THF is added dropwise dimethylazodicarboxylate. The reaction mixture is stirred at room temperature until analysis by thin layer chromatography shows that no starting material remains. The mixture is filtered through celite, and the filtrate is concentrated. The resulting yellow oil is partitioned between methylene chloride and water. The organic layer is separated, washed with water and brine, dried over MgSO$_4$, filtered and concentrated. The crude material is purified by flash column chromatography on silica gel to give the desired protected E-allylic amidine product.

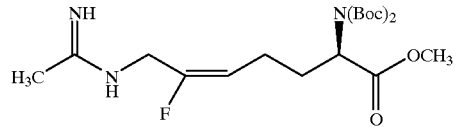

EX-5G)

The product from EX-5F is dissolved in methanol and acetic acid in water. Zinc dust is added, and the mixture is agitated under sonication until HPLC analysis shows that little of the starting material remains. The Zn dust is filtered through celite from the reaction mixture, and the filtrate is concentrated. The crude material is purified by reverse-phase HPLC column chromatography. Fractions containing product are combined and concentrated affording the desired acetamidine product as a trifluoroacetate salt.

Example 5)

A solution of EX-5G in 6.0 N HCl is refluxed for 1 h. The solvent is removed in vacuo. The resulting solid is dissolved in water and concentrated repeatedly from 1.0 N HCl to remove any remaining TFA salts to give the desired (2R, 5E)-2-amino-6-fluoro-7-[(1-iminoethyl)amino]-5-heptenoic acid, dihydrochloride product.

EXAMPLE 6

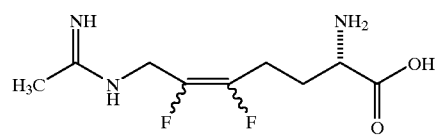

(2S,5E/Z)-2-amino-5,6-difluoro-7-[(1-iminoethyl)amino]-5-heptenoic Acid, Dihydrochloride

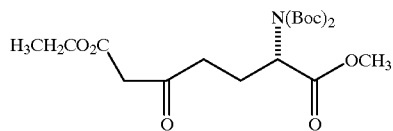

EX-6A)

To a solution of EX-1C in methylene chloride containing one equivalent of tin(II) chloride at room temperature is added ethyl diazoacetate. Immediate gas evolution is observed as the mixture is stirred at room temperature. When the reaction is complete by analysis using thin layer chromatography, the mixture is quenched with aqueous HCl, and extracted with methylene chloride. The combined organic layers are dried, filtered and purified by column chromatography to give the desired beta-ketoester product.

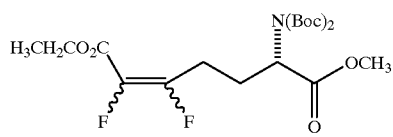

EX-6B)

A solution of the product from EX-6A in N-methyl-2-pyrolidinone is cooled to −78° C., and one equivalent of DAST is added. The resulting mixture is allowed to slowly warm to room temperature. When the reaction is complete by analysis using thin layer chromatography, the mixture is quenched and concentrated. The resulting residue is extracted with methylene chloride. The combined organic layers are dried, filtered and purified by column chromatography to give the desired difluoro olefin product as a mixture of E- and Z-isomers.

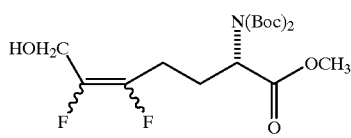

EX-6C)

To a solution of the product from EX-6B in methanol at room temperature is added solid NaBH$_4$ in portions. The reaction is stirred at ambient temperature, until analysis by thin layer chromatography shows that most of the starting material is consumed. The reaction is quenched with sat. aqueous NH$_4$Cl and extracted with ethyl acetate. The organic layers are combined, dried over MgSO$_4$, filtered and concentrated. The crude material is purified by flash column chromatography on silica gel to give the desired difluoro-allylic alcohol product as a -mixture of E- and Z-isomers.

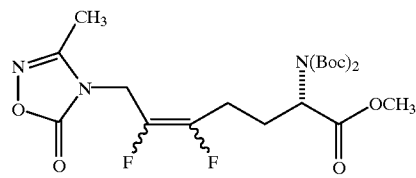

EX-6D)

To a mixture of the product from EX-6C, polymer-supported triphenylphosphine and 3-methyl-1,2,4-oxadiazolin-5-one in THF is added dropwise dimethylazodicarboxylate. The reaction is stirred at room temperature, until analysis by thin layer chromatography shows that no starting material remains. The mixture is filtered through celite, and the filtrate is concentrated. The resulting oil is partitioned between methylene chloride and water. The organic layer is separated, washed with water and brine, dried over MgSO$_4$, filtered and concentrated. The crude material is purified by flash column chromatography on silica gel to give the desired protected difluoro-allylic amidine product as a mixture of E- and Z-isomers.

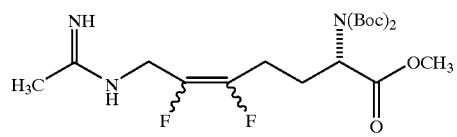

EX-6E)

To a solution of the product from EX-6D in methanol and 25% acetic acid in water, is added zinc dust, and the mixture is agitated under sonication, until HPLC analysis shows that little of the starting material remains. The zinc dust is filtered through celite from the reaction mixture, and the filtrate is concentrated. The crude material is purified by reverse-phase HPLC column chromatography. Fractions containing product are combined and concentrated affording the desired difluoro allylic acetamidine trifluoroacetate product as a mixture of E- and Z-isomers.

Example-6)

A solution of the product from EX-6E in 6.0 N HCl is refluxed for 1 h. The solvent is removed in vacuo. The resulting solid is dissolved in water and concentrated repeatedly from 1.0 N HCl to remove any remaining TFA salts. Upon completion, the desired (2S,5E/Z)-2-amino-5,6-difluoro-7-[(1-iminoethyl)-amino]-5-heptenoic acid dihydrochloride product is obtained as a mixture of E- and Z-isomers.

EXAMPLE 7

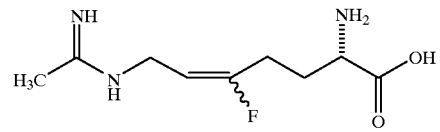

(2S,5E/Z)-2-amino-5-fluoro-7-[(1-iminoethyl)amino]-5-heptenoic acid, dihydrochloride

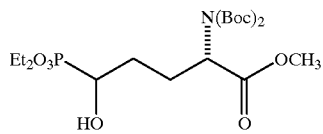

EX-7A)

A solution of the product from EX-1C and excess diethyl (trimethylsilyl)phosphite in anhydrous THF is heated at reflux until analysis by thin layer chromatography or $^{31}$P NMR indicates that no starting material remains. The solution is then cooled to room temperature and concentrated in vacuo. The resulting residue is then dissolved in aqueous methanol containing a small amount of p-toluenesulfonic acid and heated at reflux until analysis by thin layer chromatography or $^{31}$P NMR indicates that no starting material remains. The solution is cooled, concentrated and the residue is partitioned between ethyl acetate and water. The combined organics are washed with water and brine, dried over MgSO$_4$, filtered and concentrated. The crude material is purified by flash column chromatography on silica gel to give the desired hydroxymethylphosphonate product.

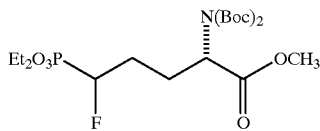

EX-7B)

To a solution of the product from EX-7A in methylene chloride pre-cooled to −78° C. is added excess DAST. The resulting mixture is stirred at −78° C., then allowed to warm slowly and stirred at room temperature until analysis by thin layer chromatography shows that no starting material remains. The reaction is quenched by the addition of a small amount of water. The organic layer is washed with water and brine, dried over MgSO$_4$, filtered and concentrated. The crude material is purified by flash column chromatography on silica gel to give the desired fluoromethylphosphonate product.

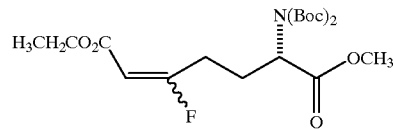

EX-7C)

To a cold (−78° C.) solution of the product from EX-7B in THF is added n-butyl lithium in hexane. This mixture is stirred at −78° C. for 20 min producing a bright yellow solution., and then is added to a cold (−78° C.) solution of ethyl glyoxalate in THF. The resulting mixture is stirred at −78° C., until analysis by thin layer chromatography shows that no starting material remains. The reaction is quenched at −78° C. with sat. aqueous NH$_4$Cl. The organic layer is collected, and the aqueous layer is extracted with diethyl ether. The combined organics are washed with water and brine, dried over MgSO$_4$, filtered and concentrated. The crude material is purified by flash column chromatography on silica gel to give the desired fluoro olefin product as a mixture of E- and Z-isomers.

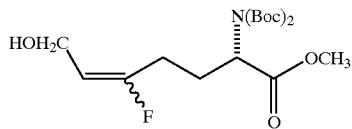

EX-7D)

To a solution of the product from EX-7C in methanol at room temperature is added solid NaBH$_4$ in portions. The reaction is stirred at ambient temperature, until analysis by thin layer chromatography shows that most of the starting material is consumed. The reaction is quenched with sat. aqueous NH$_4$Cl and extracted with ethyl acetate. The organic layers are combined, dried over MgSO$_4$, filtered and concentrated. The crude material is purified by flash column chromatography on silica gel to give the desired fluoroallylic alcohol product as a mixture of E- and Z-isomers.

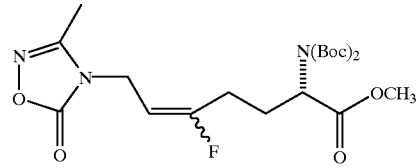

EX-7E)

To a mixture of the product from EX-7D, polymer-supported triphenylphosphine and 3-methyl-1,2,4-oxadiazolin-5-one in THF is added dropwise dimethylazodicarboxylate. The reaction is stirred at room temperature, until analysis by thin layer chromatography shows that no starting material remains. The mixture is filtered through celite, and the filtrate is concentrated. The resulting oil is partitioned between methylene chloride and water. The organic layer is separated, washed with water and brine, dried over MgSO$_4$, filtered and concentrated. The crude material is purified by flash column chromatography on silica gel to give the desired protected fluoro-allylic amidine product as a mixture of E- and Z-isomers.

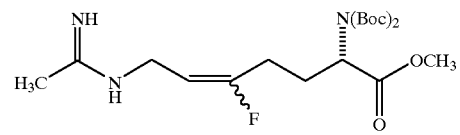

EX-7F)

To a solution of the product from EX-7E in methanol and 25% acetic acid in water, is added zinc dust, and the mixture is agitated under sonication, until HPLC analysis shows that little of the starting material remains. The zinc dust is filtered through celite from the reaction mixture, and the filtrate is concentrated. The crude material is purified by reverse-phase HPLC column chromatography. Fractions containing product are combined and concentrated affording the desired fluoro allylic acetamidine trifluoroacetate product as a mixture of E- and Z-isomers.

Example-7)

A solution of the product from EX-7F in 6.0 N HCl is refluxed for 1 h. The solvent is removed in vacuo. The resulting solid is dissolved in water and concentrated repeatedly from 1.0 N HCl to remove any remaining TFA salts. Upon completion, the desired (2S,5E/Z)-2-amino-5-fluoro-7-[(1-iminoethyl)amino]-5-heptenoic acid dihydrochloride product is obtained as a mixture of E- and Z-isomers.

EXAMPLE 8

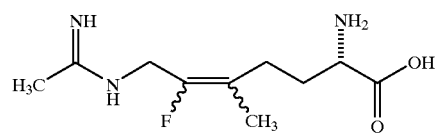

(2S,5E/Z)-2-amino-5-methyl-6-fluoro-7-[(1-iminoethyl)amino]-5-heptenoic acid, dihydrochloride

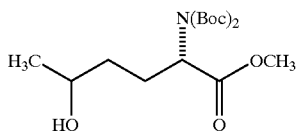

EX-8A)

To a cold solution of the product from EX-1C in anhydrous THF is added a solution of methyl Grignard reagent. The reaction is then allowed to warm slowly and stirred at room temperature until analysis by thin layer chromatography shows that no starting material remains. The reaction is quenched by the addition of a small amount of saturated aqueous ammonium chloride. The mixture is concentrated, and the residue is partitioned between ethyl acetate and water. The organic layer is washed with water and brine, dried over $MgSO_4$, filtered and concentrated. The crude material is purified by flash column chromatography on silica gel to give the desired methyl alcohol product.

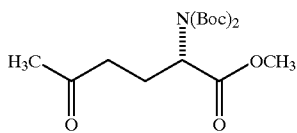

EX-8B)

To a solution of the product from EX-8A in methylene chloride at room temperature is added N-methylmorpholine-N-oxide and powdered 4A molecular sieves. The resulting mixture is then treated with tetra-n-propyl ammonium perruthenate and stirred at room temperature until analysis by thin layer chromatography shows that no starting material remains. The mixture is concentrated, and the residue is purified by flash column chromatography on silica gel to give the desired methyl ketone product.

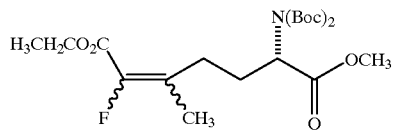

EX-8C)

To a cold (−78° C.) solution of triethyl 2-fluorophosphonoacetate in THF is added n-butyl lithium. This mixture is stirred at −78° C. producing a bright yellow solution. A solution of the product from EX-8B in THF is then added via syringe, and the resulting mixture is stirred at −78° C., until analysis by thin layer chromatography shows that no starting material remains. The reaction is then quenched at −78° C. with sat. aqueous $NH_4Cl$. The organic layer is collected, and the aqueous layer is extracted with diethyl ether. The combined organics are washed with water and brine, dried over $MgSO_4$, filtered and concentrated. The crude material is purified by flash column chromatography on silica gel to give the desired fluoro-methyl-substituted olefin product as a mixture of E- and Z-isomers.

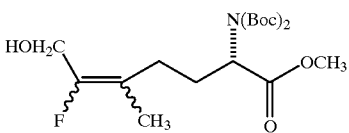

EX-8D)

To a solution of the product from EX-8C in methanol at room temperature is added solid $NaBH_4$ in portions. The reaction is stirred at ambient temperature, until analysis by thin layer chromatography shows that most of the starting material is consumed. The reaction is quenched with sat. aqueous $NH_4Cl$ and extracted with ethyl acetate. The organic layers are combined, dried over $MgSO_4$, filtered and concentrated. The crude material is purified by flash column chromatography on silica gel to give the desired fluoromethyl-substituted allylic alcohol product as a mixture of E- and Z-isomers.

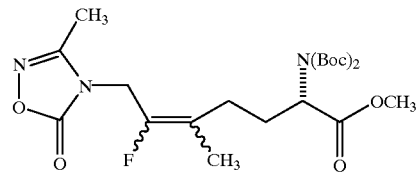

EX-8E)

To a mixture of the product from EX-8D, polymer-supported triphenylphosphine and 3-methyl-1,2,4-oxadiazolin-5-one in THF is added dropwise dimethylazodicarboxylate. The reaction is stirred at room temperature, until analysis by thin layer chromatography shows that no starting material remains. The mixture is filtered through celite, and the filtrate is concentrated. The resulting oil is partitioned between methylene chloride and water. The organic layer is separated, washed with water and brine, dried over $MgSO_4$, filtered and concentrated. The crude material is purified by flash column chromatography on silica gel to give the desired protected fluoro-methyl-substituted allylic amidine product as a mixture of E- and Z-isomers.

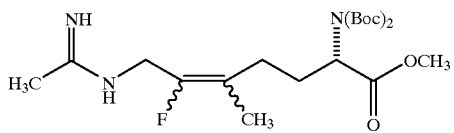

EX-8F)

To a solution of the product from EX-8E in methanol and 25% acetic acid in water, is added zinc dust, and the mixture is agitated under sonication, until HPLC analysis shows that little of the starting material remains. The zinc dust is filtered through celite from the reaction mixture, and the filtrate is concentrated. The crude material is purified by reverse-phase HPLC column chromatography. Fractions containing product are combined and concentrated affording the desired fluoro-methyl-substituted allylic acetamidine trifluoroacetate product as a mixture of E- and Z-isomers.

Example-8)

A solution of the product from EX-8F in 6.0 N HCl is refluxed for 1 h. The solvent is removed in vacuo. The resulting solid is dissolved in water and concentrated repeatedly from 1.0 N HCl to remove any remaining TFA salts.

Upon completion, the desired (2S,5E/Z)-2-amino-5-methyl-6-fluoro-7-[(1-imino-ethyl)amino]-5-heptenoic acid dihydrochloride product is obtained as a mixture of E- and Z-isomers.

EXAMPLE 9

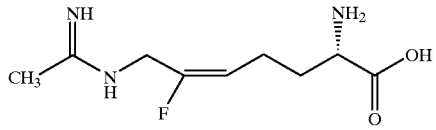

(2S,5E)-2-amino-6-fluoro-7-[(1-iminoethyl) amino]-5-heptenoic acid, dihydrochloride, monohydrate

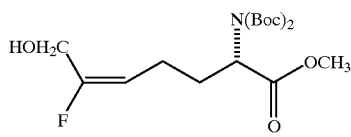

EX-9A)

To a THF (45 ml) solution of the product of EX-1C (5.0 g, 11.5 mmol) under nitrogen was added dropwise a solution of Red-Al (5.22 ml, 17.4 mmol) in 5.6 mL THF over 30 minutes.

The internal temperature was kept below −10° C. After 5 minutes, the reaction was quenched with 33.7 ml of 1.3M Na.K tartrate. Toluene (11 mL) was added to the mixture to improve separation. The organic layer was washed with 33.7 ml of 1.3M Na.K tartrate followed by brine (40 mL). The organic layers were combined, dried over MgSO4, filtered and concentrated. The crude material, 3.8 g (84%) of light yellow oil, was carried on directly into the next step. LCMS: m/z=414.2 [M+Na]$^+$. $^1$H NMR (CDCl$_3$) δ 1.48 (s, 18H), 1.95 (m, 1H), 2.1 (m, 1H), 2.2 (m, 1H), 2.35 (t, 1H), 3.7 (s, 3H), 4.25 (m, 2H), 4.8 (m, 1H), 5.15 (dt, 1H, J=20 Hz). $^{19}$F NMR (CDCl$_3$) δ −119.1 (d, 0.02F, J=37 Hz, 2% Z-isomer), −111.8 (d, 0.98F, J=24 Hz, 98% E-isomer).

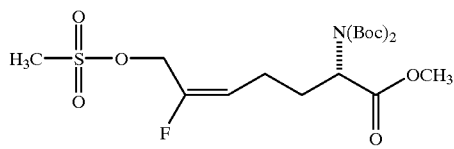

EX-9B)

To a solution of the product of EX-9A (50.0 g, 0.128 mol) in 500 mL of methylene chloride at −10° C. was added triethylamine (18.0 g, 0.179 mol). A solution of methanesulfonyl chloride (17.5 g, 0.153 mol) in 50 mL methylene chloride was added slowly to maintain temperature at −10° C. The reaction was stirred for 45 min at −10° C., at which time analysis by thin layer chromatography (50% ethyl acetate in hexane) and LCMS showed that most of the starting material was consumed. The reaction was quenched with 600 mL of 1.0 M citric acid and extracted with ethyl acetate (2×400 mL). The organic layers were combined, dried over MgSO$_4$, filtered and concentrated. The crude material, 70 g of yellow oil, was carried directly into the next step. LCMS: m/z=492.2 [M+Na].

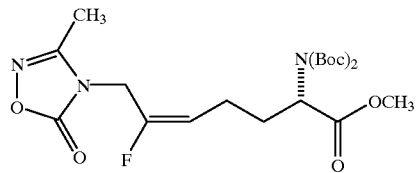

EX-9C)

To a solution of the product of EX-19B (70.0 g, 0.128 mol) in 400 mL of dimethyl formamide at room temperature was added potassium 3-methyl-1,2,4-oxadiazolin-5-onate (28.7 g, 0.192 mol). The reaction was stirred for 2.5 h at room temperature, at which time analysis by thin layer chromatography (30% ethyl acetate in hexane) and LCMS showed that the starting material was consumed. The reaction was diluted with 400 mL of water and extracted with ethyl acetate (5×400 mL). The organic layers were combined, washed with 400 mL water, 400 mL brine, dried over MgSO$_4$, filtered and concentrated. The crude material, 70 g of yellow oil, was purified by flash column chromatography on silica gel eluting with 1:4 ethyl acetate in hexane to give 38 g (63%) of a slightly yellow oil.

EX-9D)

A combination of product of several duplicate preparations of EX-9C was purified by HPLC column chromatography on Merk silica gel MODCOL column at a flow of 500 mL/min isocratic at 60:40 MtBE:heptane. A second purification on the 63 g recovered was a chiral HPLC column chromatography on a Chiral Pak-AD column runmning at a flow of 550 mL/min isocratic at 10:90 A:B (A: 100% ethanol, B: 100% heptane). Fractions containing product were combined and concentrated affording 41 g (68%) of the desired protected L,E-allylic amidine product as a clear oil, that contained only the desired L and E-isomer by $^{19}$F NMR and chiral chromatography. LCMS: m/z=496.2 [M+Na]$^+$. [M+NH$_4$]$^+$. HRMS calcd. for C$_{21}$H$_{32}$FN$_3$O$_8$: 491.2507 [M+NH$_4$]$^+$, found: 491.2517. $^1$H NMR (CDCl$_3$) δ 1.48 (s, 18H), 1.85 (m, 1H), 2.2 (m, 3H), 2.25 (s, 3H), 3.64 (s, 3H), 4.25 (m, 2H), 4.8 (m, 1H), 5.3 (dt, 1H, J=20 Hz). $^{19}$F NMR (CDCl$_3$) δ −110.8 (q, 1F, J=20 Hz).

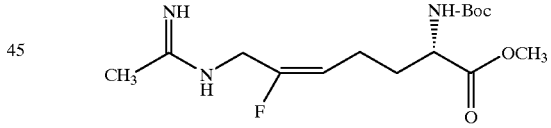

EX-9E)

The product from EX-9D (22.5 g, 0.047 mol) was dissolved in 112 mL of methanol. Vigorous stirring was begun and 225 mL of 40% acetic acid in water followed by zinc dust (11.5 g, 0.177 mmol) was added. The stirring reaction was placed under reflux (approx. 60° C.) for 2.5 h, at which time HPLC analysis showed that most of the starting material had been consumed. The reaction was cooled and the Zn was filtered from the reaction mixture through celite, washing the celite well with additional methanol. The filtrate and methanol washings were combined and concentrated. The resulting oily-white solid was washed with methylene chloride (2×500 mL) and filtered through a celite pad, an additional 500 mL methylene chloride wash was performed. The filtrates were combined and concentrated to provide a light yellow oil. The crude material, 39 g of a light-yellow oil, was purified by plug filtration on 200 mL silica gel eluting with 80:19:1 methanol: methylene chloride: acetic acid to give 13 g (83%) of the desired product. LCMS: m/z=432.3 [M+H]$^+$. 1 [M+H]$^+$. HRMS calcd. for $C_{15}H_{26}FN_3O_4$: 332.1986 [M+H]$^+$, found: 332.1982. $^1$H NMR (CD$_3$OD) δ 1.42 (s, 9H), 1.7 (m, 1H), 1.9 (m, 1H), 2.17 (m, 2H), 2.22 (s, 3H), 3.3 (m, 1H), 3.7 (s, 3H), 4.2 (d, 2H), 5.1 (dt, vinyl, 1H, J=21 Hz). $^{19}$F NMR (CD$_3$OD) δ −110.83 (m, 1F, J=21 Hz).

Example 9)

A solution of the product of EX-1E (22 g, 0.066 mol) in 750 mL of 6.0 N HCl was refluxed for 45 min. The solvent was removed in vacuo. The resulting solid was dissolved in water and concentrated three additional times. The crude material was purified by reverse-phase HPLC column chromatography on a YMC ODS-AQ column eluting over 60 min pumping 100% isocratic B for 30 min followed by a gradient of 0–100% A for 10 min and a 100% A wash for 20 min (A: 100% acetonitrile, B: 100% H$_2$O with 0.0025% acetic acid). Fractions containing product were combined and concentrated affording 3.5 g (68%) of the desired acetamidine product as a dihydorchloride salt, that contained only the desired (2S,5E)-2-amino-6-fluoro-7-[(1-iminoethyl)amino]-5-heptenoic acid, dihydrochloride product was obtained as a white solid, m.p. 51.5–56.3° C., that contained only the desired E-isomer by $^{19}$F NMR. LCMS: m/z=218.1 [M+H]$^+$. HRMS calcd. for $C_9H_{16}FN_3O_2$: 218.1305 [M+H]$^+$, found: 218.1325. $^1$H NMR (D$_2$O) δ 1.8 (m, 2H), 2.05 (m, 2H), 2.1 (s, 3H), 3.7 (t, 1H), 4.00 (d, 2H), 5.3 (dt, vinyl, 1H, J=21 Hz). $^{19}$F NMR (D$_2$O) δ −109.9 (m, 1F, J=20 Hz). [α]$_{589}$=+15.3 (C, 0.334, (H$_2$O); ). [α]$_{365}$=+52.8 (C, 0.334, (H$_2$O)

EXAMPLE 10

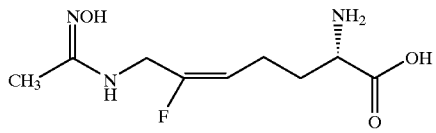

(2S,5E)-2-amino-6-fluoro-7-[(1-hydroximinoethyl)amino]-5-heptenoic acid

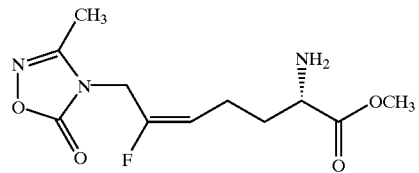

EX-10A)

Gaseous HCl was bubbled for 5 min through a stirring cold (0° C.) solution of the product of EX-9C (14 g, 30.0 mmol) in 100 mL of methanol. The resulting dark yellow solution was stirred an additional 30 min, at which time HPLC indicated complete consumption of starting material. The resulting mixture was neutralized with saturated NaHCO$_3$ to pH=8, and the product was extracted out with EtOAc. The organic layer was dried over MgSO$_4$ and concentrated to give the desired amino ester product as a dark yellow oil that was carried on crude to the next step. LCMS: m/z=274 [M+Na]$^+$. $^1$H NMR (CDCl$_3$) δ 1.8 (m, 4H), 2.25 (s, 3H), 3.42 (bm, 1H), 3.80 (s, 3H), 4.4 (dd, 2H), 5.40 (dt, vinyl, 1H, J=21 Hz). $^{19}$F NMR (CDCl$_3$) δ −110.38 (m, 1F, J=21 Hz).

Example 10)

A solution of the product of EX-10A (8 g, 30 mmol) in 70 mL of 2.5N NaOH was stirred for 10 min, at which time HPLC analysis indicated the complete consumption of starting material. The resulting solution was neutralized with 12N HCl (approximately 50 mL) to pH=7–8 and concentrated. The resulting slurry was washed with methanol, filtered to remove salts and concentrated to a brownish oil. The crude material was purified by reverse-phase HPLC column chromatography on a YMC ODS-AQ column eluting over 60 min pumping 100% isocratic B for 30 min followed by a gradient of 0–100% A for 10 min and a 100% A wash for 20 min (A: 100% acetonitrile, B: 100%). Fractions containing product were combined and concentrated affording 1.0 g (14%) of the desired product as a white solid. The product was recrystallized from hot water and isopropyl alcohol and collected by filtration to afford pure (2S,5E)-2-amino-6-fluoro-7-[(1-hydroximinoethyl)amino]-5-heptenoic acid as a white crystalline solid. Melting point: 198.00–200.00° C. LCMS: m/z=234.1 [M+H]$^+$. $^1$H NMR (D$_2$O) δ 1.8 (m, 4H), 2.05 (m, 2H), 3.6 (t, 1H), 3.9 (d, 2H), 5.2 (dt, vinyl, 1H, J=21 Hz). $^{19}$F NMR (D$_2$O) δ −112.1 (m, 1F, J=20 Hz).). Anal. calcd. for $C_9H_{16}FN_3O_3$: C, 46.35; H, 6.91; N, 18.02; 0, 20.58. Found: C, 46.44; H, 6.95; N, 17.94; 0, 20.78. Chiral analysis >97.7%: CrownPak CR(+) at 0.8 mL/min isocratic with 100% A (A: aqueous HClO$_4$, pH=1.5).

EXAMPLE 11

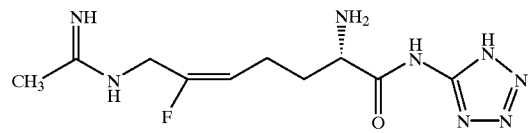

(2S,5E)-2-amino-6-fluoro-7-[(1-iminoethyl)amino]-N-(1H-tetrazol-5-yl) 5-heptenamide, dihydrochloride

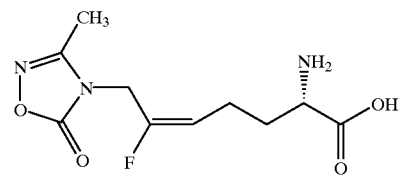

EX-11A)

The product from EX-9C (6.1 g, 0.013 mol) was dissolved in 4 mL of methanol. Vigorous stirring was begun and 10 mL of 6N HCl was added. The stirring reaction was placed under reflux (approx. 60° C.) for 18 h, at which time HPLC analysis showed that most of the starting material had been consumed. The reaction was cooled and concentrated to 3.3 g (100%) of orange oil. LCMS: m/z=282 [M+Na]$^+$.

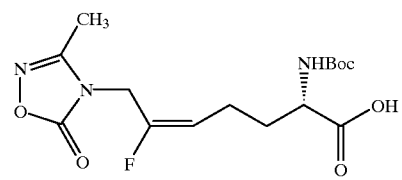

EX-11B)

The product from EX-11A (3.3 g, 0.013 mol) was dissolved in 12 mL of 1:1 H$_2$O:dioxane. Stirring was begun and triethylamine (1.95 g, 0.019 mol) was added. The reaction was cooled to 0° C. and di-tert-butyldicarbonate (3.4 g, 0.016 mol) was added. The reaction was allowed to warm to room temperature at which time acetonitrile (4 mL) was added to dissolve solids. The reaction was stirred at room temperature for 18 h at which time HPLC analysis showed that most of the starting material had been consumed. The reaction was quenched with 1.0N KHSO$_4$ (25 mL), extracted with ethyl acetate (3×50 mL) and the organic layers dried over MgSO$_4$ and concentrated. The crude material, 3.5 g of a dark oil, was purified by flash chromatography eluting with 4:95:1 methanol: methylene chloride: acetic acid to give 2.4 g (52%) of desired product as a light-yellow oil. LCMS: m/z=382 [M+Na]$^+$.

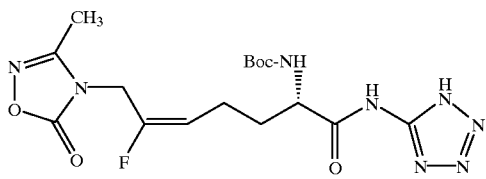

EX-11C)

The product from EX-11B (2.4 g, 0.007 mol) was dissolved in 13 mL THF. Stirring was begun and 5-aminotetrazole monohydrate (0.83 g, 0.008 mol) was added followed by 1,3-diisopropylcarbodiimide (1.0 g, 0.008 mol). The resulting mixture was allowed to stir at room temperature for 3 h at which time HPLC showed that most of the starting material had been consumed. To the reaction was added 12 mL water and the THF was removed by vaccum distillation. Ethanol (30 mL) was added and the reaction was heated to reflux. After 15 min at reflux, the reaction was cooled to −10° C. at which time the desired product precipitated from solution. The product was collected by filtration to afford 1.25 g (50%) of a white solid. LCMS: m/z=449 [M+Na]$^+$.

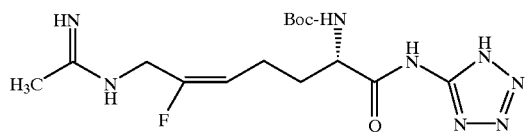

EX-11D)

The product from EX-11C (1.0 g, 0.0023 mol) was dissolved in 5 mL of methanol. Vigorous stirring was begun and 10 mL of 40% acetic acid in water followed by zinc dust (0.5 g, 0.008 mol) was added. The stirring reaction was placed under reflux (approx. 60° C.) for 1.5 h, at which time HPLC analysis showed that most of the starting material had been consumed. The reaction was cooled and the Zn was filtered from the reaction mixture through celite, washing the celite well with additional methanol. The filtrate and methanol washings were combined and concentrated. The resulting oily-white solid was purified by reverse-phase HPLC column chromatography on a YMC ODS-AQ column eluting over 60 min pumping 100% isocratic B for 30 min followed by a gradient of 0–100% A for 10 min and a 100% A wash for 20 min (A: 100% acetonitrile, B: 100% H$_2$O with 0.0025% acetic acid). Fractions containing product were combined and concentrated affording 0.390 g (44%) of the desired acetamidine product as a white solid. LCMS: m/z=407.3 [M+Na].

Example 11)

The product from EX-11D (0.30 g, 0.780 mmol) was dissolved in 5 mL of conc HOAc. To this was added 1 mL of 4N HCl in dioxane. The reaction was stirred 5 min. at room temperature. The solvent was removed in vacuo. The resulting solid was dissolved in water and concentrated three additional times. HPLC indicated amounts of starting material. The solid was dissolved in 1N HCl and stirred 3h at which time HPLC indicated that most of the starting material had been consumed. The solution was concentrated affording 290 mg (98%) of the desired acetamidine product as a dihydorchloride salt. LCMS: m/z=285.1 [M+H].

Biological Data

Some or all of the following assays are used to demonstrate the nitric oxide synthase inhibitory activity of the invention's compounds as well as demonstrate the useful pharmacological properties.

Rat Carrageenan Foot Pad Edema Test

The carrageenan foot edema test is a useful assay for evaluating anti-inflammaory properties of compounds of the present invention. The carrageenan foot edema test is performed with materials, reagents and procedures essentially as described by Winter, et al., (*Proc. Soc. Exp. Biol. Med.*, 111, 544 (1962)). Male Sprague-Dawley rats are selected in each group so that the average body weight is as close as possible. Rats are fasted with free access to water for over sixteen hours prior to the test. The rats are dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline is administered and the volume of the injected foot is measured with a displacement plethysmometer connected to a pressure transducer with a digital indicator. Three hours after the injection of the carrageenan, the volume of the foot is again measured. The average foot swelling in a group of drug-treated animals is compared with that of a group of placebo-treated animals and the percentage inhibition of edema is determined (Ottemess and Bliven, *Laboratory Models for Testing NSAIDs*, in *Non-steroidal Anti-Inflammatory Drugs*, (J. Lombardino, ed. 1985)). The percent inhibition shows the percentage decrease from control paw volume determined in this procedure.

Citrulline Assay for Nitric Oxide Synthase

Nitric oxide synthase (NOS) activity can be measured by monitoring the conversion of L-[2,3-$^3$H]-arginine to L-[2, 3-$^3$H]-citrulline (Bredt and Snyder, *Proc. Natl. Acad. Sci. U.S.A.*, 87, 682–685, 1990 and Moore et al, *J. Med. Chem.*, 39, 669–672, 1996). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a λcDNA library made from RNA extracted from a colon sample from a patient with ulcerative colitis. The cDNA for human endothelial constitutive NOS (hecNOS) is isolated from a λcDNA library made from RNA extracted from human umbilical vein endothelial cells (HUVEC) and the cDNA for human neuronal constitutive NOS (hncNOS) is isolated from a λcDNA library made from RNA extracted from human cerebellum obtained from a cadaver. The recombinant enzymes are expressed in Sf9 insect cells using a baculovirus vector (Rodi et al, in *The Biology of Nitric Oxide, Pt. 4: Enzymology, Biochemistry and Immunology*: Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 μL of enzyme is added to 40 μL of 50 mM Tris (pH 7.6) in the presence or absence of test compounds and the reaction initiated by the addition of 50 μL of a reaction mixture containing 50 mM Tris (pH 7.6), 2.0 mg/mL bovine serum albumin, 2.0 mM DTT, 4.0 mM CaCl$_2$, 20 μM FAD, 100 μM tetrahydrobiopterin, 0.4 mM NADPH and 60 μM L-arginine containing 0.9 μCi of L-[2,3-$^3$H]-arginine. The final concentration of L-arginine in the assay is 30 μM. For hecNOS or hncNOS, calmodulin is included at a final concentration of 40–100 mM. Following incubation at 37° C. for 15 minutes, the reaction is terminated by addition of 400 μL of a suspension (1 part resin, 3 parts buffer) of Dowex 50W X-8 cation exchange resin in a stop buffer containing 10 mM EGTA, 100 mM HEPES, pH 5.5 and 1 mM L-citrulline. After mixing the resin is allowed to settle and L-[2,3-$^3$H]-Citrulline formation is determined by counting aliquots of the supernatant with a liquid scintillation counter. Results are reported in Table I as the IC$_{50}$ values of compounds for hiNOS, hecNOS and hncNOS.

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 15–45 mg in weight and one or two explants per well are placed into either 96 or 48 well culture plates with 200–500 μL of culture media per well. The culture media was either a custom modification of Minimum Essential Medium(Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 μM L-Arginine (Sigma), 2 mM L-glutamine, 1X HL-1 supplement (BioWhittaker), 50 mg/ml ascorbic acid (Sigma) and 150 μg/ml recombinant human IL-1β (RD Systems) to induce nitric oxide synthase. Compounds are then added in 10 μL aliquots and the explants incubated at 37° C. with 5% CO$_2$ for 18–24 hours. The day old supernatant is then discarded and replaced with fresh culture media containing recombinant human IL-1β and compound and incubated for another 20–24 hours. This supernatant is analyzed for nitrite with a fluorometric assay (Misko et al, Anal. Biochem., 214, 11–16, 1993). All samples are done in quadruplicate. Unstimulated controls are cultured in media in the absence of recombinant human IL-1β. IC$_{50}$ values (Table I) are determined from plotting the percent inhibition of nitrite production at six different concentrations of inhibitor.

TABLE I

| Example Number | IC$_{50}$ [μM] | | | |
|---|---|---|---|---|
| | hiNOS | hecNOS | hncNOS | Human cartilage |
| 1 | 0.36 | 68 | 3.6 | 0.1 |
| 2 | 2.2 | 195 | 21 | 0.2 |
| 3 | 12 | 303 | 105 | |
| 4 | 8.6 | 112 | 65 | 2.5 |
| 5 | <5 | 279 | 29 | |

In Vivo Assay

Rats can be treated with an intraperitoneal injection of 1–12.5 mg/kg of endotoxin (LPS) with or without oral administration of the nitric oxide synthase inhibitors. Plasma nitrite/nitrate levels can be determined 5 hours post-treatment. The results can be used to show that the administration of the nitric oxide synthase inhibitors decreases the rise in plasma nitrite/nitrate levels, a reliable indicator of the production of nitric oxide induced by endotoxin. As shown in Table II, Example 1 ((2S,5E)-2-amino-6-fluoro-7-[(1 iminoethyl)amino]-5-heptenoic acid, dihydrochloride) inhibited the LPS-induced increase in plasma nitrite/nitrate levels with an observed ED$_{50}$ value of <0.1 mg/kg, demonstrating the ability to inhibit inducible nitric oxide synthase activity in vivo.

TABLE II

ED$_{50}$'s for Compounds Determined in Endotoxin-Treated Rats
All compounds administered orally unless otherwise noted.

| Compound | ED$_{50}$ (mg/kg) |
|---|---|
| Example 1 | <0.1 |
| Example 4 | >10 |
| Example 10 | <0.1 |
| Example 11 | <0.3 |

Raw Cell Nitrite Assay

RAW 264.7 cells can be plated to confluency on a 96-well tissue culture plate grown overnight (17 h) in the presence of LPS to induce NOS. A row of 3–6 wells can be left untreated and served as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 μL of buffer containing L-arginine (30 μM) +/– inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite. T. P. Misko et al, Analytical Biochemistry, 214, 11–16 (1993).

What is claimed is:

1. A compound having a structure corresponding to Formula I:

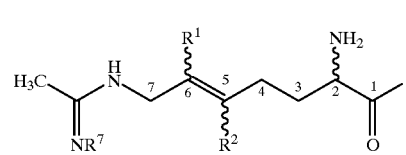

or a pharmaceutically acceptable salt thereof, wherein:
R$^1$ is selected from the group consisting of H, halo and alkyl which is optionally substituted by one or more halo;
R$^2$ is selected from the group consisting of H, halo and alkyl which is optionally substituted by one or more halo;
with the proviso that at least one of R$_1$ or R$_2$ contains a halo;
R$^7$ is selected from the group consisting of H and hydroxy; and
J is selected from the group consisting of hydroxy, alkoxy, and NR$^3$R$^4$ wherein;
R$^3$ is selected from the group consisting of H, lower alkyl, lower alkylenyl and lower alkynyl; and
R$^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

2. The compound of claim 1 having a structure corresponding to Formula II

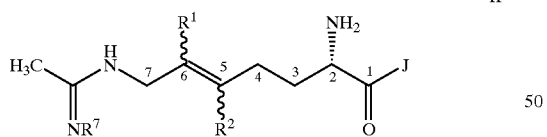

or a pharmaceutically acceptable salt thereof, wherein:
$R^1$ is selected from the group consisting of H, halo and alkyl which is optionally substituted by one or more halo;
$R^2$ is selected from the group consisting of H, halo and alkyl which is optionally substituted by one or more halo;
with the proviso that at least one of $R_1$ or $R_2$ contains a halo;
$R^7$ is selected from the group consisting of H and hydroxy; and
J is selected from the group consisting of hydroxy, alkoxy, and $NR^3R^4$ wherein;
$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

3. The compound of claim 1 having a structure corresponding to Formula III:

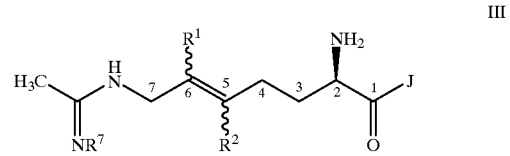

or a pharmaceutically acceptable salt thereof, wherein:
$R^1$ is selected from the group consisting of H, halo and alkyl which is optionally substituted by one or more halo;
$R^2$ is selected from the group consisting of H, halo and alkyl which is optionally substituted by one or more halo;
with the proviso that at least one of $R^1$ or $R^2$ contains a halo;
$R^7$ is selected from the group consisting of H and hydroxy; and
J is selected from the group consisting of hydroxy, alkoxy, and $NR^3R^4$ wherein;

R³ is selected from the group consisting of H, lower alkyl, lower alkylenyl and lower alkynyl; and R⁴ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkyphosphonoalkyl, diaralkoxyphosphonoalkyl, guanidino, amidino, and acylamino.

4. The compound of claim 1 wherein:
R¹ is selected from the group consisting of H and $C_1$–$C_3$ alkyl which is optionally substituted by one or more halo; and
R² is fluorine.

5. The compound of claim 1 wherein:
R¹ is H; and
R² is fluorine.

6. The compound of claim 1 wherein:
R¹ is halo; and
R² is halo.

7. The compound of claim 1 wherein:
R¹ is fluorine; and
R² is fluorine.

8. The compound of claim 1 wherein:
R¹ is fluorine ; and
R² is selected from the group consisting of H and $C_1$–$C_3$ alkyl which is optionally substituted by one or more halo.

9. The compound of claim 1 wherein:
R¹ is fluorine; and
R² is H.

10. The compound of claim 1 wherein said compound is the E isomer.

11. The compound of claim 1 wherein said compound is the Z isomer.

12. The compound of claim 1 wherein said compound is the R enantiomer at the 2-position.

13. The compound of claim 1 wherein said compound is the S enantiomer at the 2-position.

14. The compound of claim 1 wherein the compound is in the form of a pharmaceutically-acceptable salt.

15. The pharmaceutically-acceptable salt of claim 14 having at least one anionic counterion.

16. The pharmaceutically-acceptable salt of claim 15 wherein the anionic counterion is selected from the group consisting of a halide, a carboxylate, a sulfonate, a sulfate, a phosphate, a phosphonate, a resin-bound anion, and a nitrate.

17. The pharmaceutically-acceptable salt of claim 16 wherein the anionic counterion is a halide.

18. The pharmaceutically-acceptable salt of claim 17 wherein the halide is chloride.

19. The pharmaceutically-acceptable salt of claim 16 wherein the anionic counterion is a carboxylate.

20. The pharmaceutically-acceptable salt of claim 19 wherein the carboxylate is selected from the group consisting of formate, acetate, propionate, trifluoroacetate, succinate, salicylate, DL-aspartate, D-aspartate, L-aspartate, DL-glutamate, D-glutamate, L-glutamate, glycerate, succinate, steric, DL-tartarate, D-tartarate, L-tartarate, (±)-mandelate, (R)-(–)-mandelate, (S)-(+)-mandelate, citrate, mucate, maleate, malonate, benzoate, DL-malate, D-malate, L-malate, hemi-malate, 1-adamantaneacetate, 1-adamantanecarboxylate, flavianate, sulfonoacetate, (±)-lactate, L-(+)-lactate, D-(–)-lactate, pamoate, D-alpha-galacturonate, glycerate, DL-cystate, D-cystate, L-cystate, DL-homocystate, D-homocystate, L-homocystate, DL-cysteate, D-cysteate, L-cysteate, (4S)-hydroxy-L-proline, cyclopropane-1,1-dicarboxylate, 2,2-dimethylmalonate, squarate, tyrosine anion, proline anion, fumarate, 1-hydroxy-2-naphthoate, phosphonoacetate, carbonate, bicarbonate, 3-phosphonopropionate, DL-pyroglutamate, D-pyroglutamate, and L-pyroglutamate.

21. The pharmaceutically-acceptable salt of claim 16 wherein the anionic counterion is a sulfonate.

22. The pharmaceutically-acceptable salt of claim 21 wherein the sulfonate is selected from the group consisting of methanesulfonate, toluenesulfonate, benzenesulfonate, trifluoromethylsulfonate, ethanesulfonate, (±)-camphorsulfonate, naphthalenesulfonate, 1R-(–)-camphorsulfonate, 1S-(+)-camphorsulfonate, 2-mesitylenesulfonate, 1,5-naphthalenedisulfonate, 1,2-ethanedisulfonate, 1,3-propanedisulfonate, 3-(N-morpholino)propane sulfonate, biphenylsulfonate, isethionate, and 1-hydroxy-2-naphthalenesulfonate.

23. The pharmaceutically-acceptable salt of claim 16 wherein the anionic counterion is a sulfate.

24. The pharmaceutically-acceptable salt of claim 23 wherein the sulfate is selected from the group consisting of sulfate, monopotassium sulfate, monosodium sulfate, and hydrogen sulfate.

25. The pharmaceutically-acceptable salt of claim 16 wherein the anionic counterion is a phosphate.

26. The pharmaceutically-acceptable salt of claim 26 wherein the phosphate is selected from the group consisting of phosphate, dihydrogen phosphate, potassium hydrogen phosphate, dipotassium phosphate, potassium phosphate, sodium hydrogen phosphate, disodium phosphate, sodium phosphate, calcium phosphate, and hexafluorophosphate.

27. The pharmaceutically-acceptable salt of claim 16 wherein the anionic counterion is a phosphonate.

28. The pharmaceutically-acceptable salt of claim 27 wherein the phosphonate is selected from the group consisting of vinylphosphonate, 2-carboxyethylphosphonate and phenylphosphonate.

29. The pharmaceutically-acceptable salt of claim 16 wherein the anionic counterion is a resin-bound anion.

30. The pharmaceutically-acceptable salt of claim 29 wherein the resin-bound anion is selected from the group consisting of a resin comprising polyacrylate and a resin comprising sulfonated poly(styrene divinylbenzene).

31. The pharmaceutically-acceptable salt of claim 16 wherein the anionic counterion is nitrate.

32. The pharmaceutically-acceptable salt of claim 15 wherein the anion is selected from the group consisting of DL-ascorbate, D-ascorbate, and L-ascorbate.

33. The pharmaceutically-acceptable salt of claim 14 having at least one cationic counterion.

34. The pharmaceutically-acceptable salt of claim 33 wherein the cationic counterion is selected from the group consisting of an ammonium cation, a alkali metal cation, an alkaline earth metal cation, a transition metal cation, and a resin-bound cation.

35. The pharmaceutically-acceptable salt of claim 34 wherein the cationic counterion is an ammonium cation.

36. The pharmaceutically-acceptable salt of claim 35 wherein the ammonium cation is selected from the group consisting of ammonium, methyl ammonium, dimethylammonium, trimethylammonium, tetramethylammonium, ethanolammonium, dicyclohexylammonium, guanidinium, and ethylenediammonium cation.

37. The pharmaceutically-acceptable salt of claim 34 wherein the cationic counterion is an alkali metal cation.

38. The pharmaceutically-acceptable salt of claim 37 wherein the alkali metal cation is selected from the group consisting of lithium cation, sodium cation, potassium cation, and cesium cation.

39. The pharmaceutically-acceptable salt of claim 34 wherein the cationic counterion is an alkaline earth metal cation.

40. The pharmaceutically-acceptable salt of claim 39 wherein the alkaline earth metal cation is selected from the group consisting of beryllium cation, magnesium cation, and calcium cation.

41. The pharmaceutically-acceptable salt of claim 34 wherein the cationic counterion is a transition metal cation.

42. The pharmaceutically-acceptable salt of claim 41 wherein the transition metal cation is a zinc cation.

43. The pharmaceutically-acceptable salt of claim 34 wherein the cationic counterion is a resin-bound cation.

44. The pharmaceutically-acceptable salt of claim 43 wherein the resin-bound cation is a cationically functionalized poly(styrene divinylbenzene) resin.

45. The pharmaceutically-acceptable salt of claim 44 wherein the resin-bound cation is an aminated poly(styrene divinylbenzene) resin.

46. The pharmaceutically-acceptable salt of claim 43 wherein the resin-bound cation is a cationically functionalized polyacrylic resin.

47. The pharmaceutically-acceptable salt of claim 43 wherein the resin-bound cation is an aminated polyacrylic resin.

48. A compound having the structure corresponding to Formula IV:

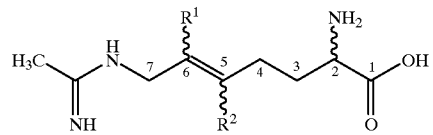

or a pharmaceutically acceptable salt thereof, wherein:
$R^1$ is selected from the group consisting of H, halo and alkyl which is optionally substituted by one or more halo;
$R^2$ is selected from the group consisting of H, halo and alkyl which is optionally substituted by one or more halo; and
with the proviso that at least one of $R^1$ or $R^2$ contains a halo.

49. The compound of claim 48 wherein:
$R^1$ is halo; and
$R^2$ is selected from the group consisting of H, halo and alkyl wherein said alkyl is optionally substituted by one or more halo.

50. The compound of claim 48 wherein:
$R^1$ is halo; and
$R^2$ is selected from the group consisting of H, F, and $C_1$–$C_3$ alkyl, wherein said $C_1$–$C_3$ alkyl is optionally substituted by one or more halo.

51. The compound of claim 48 wherein:
$R^1$ is fluorine; and
$R^2$ is selected from the group consisting of H and $C_1$–$C_3$ alkyl, said $C_1$–$C_3$ alkyl optionally substituted by one or more halo.

52. The compound of claim 48 wherein:
$R^1$ is selected from the group consisting of H and $C_1$–$C_3$ alkyl, said $C_1$–$C_3$ alkyl; and
$R^1$ is fluorine.

53. The compound of claim 48 wherein:
$R^1$ is H; and
$R^2$ is fluorine.

54. The compound of claim 48 wherein said compound is the E isomer.

55. The compound of claim 48 wherein said compound is the Z isomer.

56. The compound of claim 48 wherein said compound is the R enantiomer at the 2 position.

57. The compound of claim 48 wherein said compound is the S enantiomer at the 2 position.

58. A compound selected from the group consisting of:
(2S,5E)-2-amino-6-fluoro-7-[(1-iminoethyl)amino]-5-heptenoic acid;
(2S,5E/Z)-2-amino-6-fluoro-7-[(1-iminoethyl)amino]-5-heptenoic acid;
(2S,5Z)-2-amino-6-fluoro-7-[(1-iminoethyl)amino]-5-heptenoic acid;
(2S,5Z)-2-amino-6-fluoro-7-[(1-iminoethyl)amino]-5-heptenoic acid;
(2R,5E)-2-amino-6-fluoro-7-[(1-iminoethyl)amino]-5-heptenoic acid,;
(2S,5E/Z)-2-amino-5,6-difluoro-7-[(1-iminoethyl)amino]-5-heptenoic acid;
(2S,5E/Z)-2-amino-5-fluoro-7-[(1-iminoethyl)amino]-5-heptenoic acid;

(2S,5E/Z)-2-amino-5-methyl-6-fluoro-7-[(1-iminoethyl)
   amino]-5-heptenoic acid;
(2S,5E)-2-amino-5,6-difluoro-7-[(1-iminoethyl)amino]-
   5-heptenoic acid;
(2S,5Z)-2-amino-5,6-difluoro-7-[(1-iminoethyl)amino]-
   5-heptenoic acid;
(2S,5E)-2-amino-6-fluoro-7-[(1-iminoethyl)amino]-N-(1
   H-tetrazol-5-yl) 5-heptenamide,
(2S,5E)-2-amino-6-fluoro-7-[(1-iminoethyl)amino]-5-
   heptenoic acid, dihydrochloride, monohydrate;
(2S,5E/Z)-2-amino-6-fluoro-7-[(1-iminoethyl)amino]-5-
   heptenoic acid, dihydrochloride;
(2S,5Z)-2-amino-6-fluoro-7-[(1-iminoethyl)amino]-5-
   heptenoic acid, dihydrochloride;
(2S,5Z)-2-amino-6-fluoro-7-[(1-iminoethyl)amino]-5-
   heptenoic acid, trihydrochloride, dihydrate;
(2R,5E)-2-amino-6-fluoro-7-[(1-iminoethyl)amino]-5-
   heptenoic acid, dihydrochloride, monohydrate;
(2S,5E/Z)-2-amino-5,6-difluoro-7-[(1-iminoethyl)
   amino]-5-heptenoic acid, dihydrochloride;
(2S,5E/Z)-2-amino-5-fluoro-7-[(1-iminoethyl)amino]-5-
   heptenoic acid, dihydrochloride;
(2S,5E/Z)-2-amino-5-methyl-6-fluoro-7-[(1-iminoethyl)
   amino]-5-heptenoic acid, dihydrochloride;
(2S,5E)-2-amino-5,6-difluoro-7-[(1-iminoethyl)amino]-
   5-heptenoic acid, dihydrochloride;
(2S,5Z)-2-amino-5,6-difluoro-7-[(1-iminoethyl)amino]-
   5-heptenoic acid, dihydrochloride; and
(2S,5E)-2-amino-6-fluoro-7-[(1-iminoethyl)amino]-N-
   (1H-tetrazol-5-yl) 5-heptenamide, dihydrochloride.

59. (2S,5E)-2-amino-6-fluoro-7-[(1-iminoethyl)amino]-5-heptenoic acid.

60. (2S,5E/Z)-2-amino-6-fluoro-7-[(1-iminoethyl)amino]-5-heptenoic acid.

61. (2S,5Z)-2-amino-6-fluoro-7-[(1-iminoethyl)amino]-5-heptenoic acid.

62. (2S,5E/Z)-2-amino-5-fluoro-7-[(1-iminoethyl)amino]-5-heptenoic acid.

63. (2S,5E/Z)-2-amino-5-methyl-6-fluoro-7-[(1-iminoethyl)amino]-5-heptenoic acid.

64. (2R,5E)-2-amino-6-fluoro-7-[(1-iminoethyl)amino]-5-heptenoic acid.

65. (2S,5E/Z)-2-amino-5,6-difluoro-7-[(1-iminoethyl)amino]-5-heptenoic acid.

66. (2S,5E)-2-amino-6-fluoro-7-[(1-iminoethyl)amino]-N-(1H-tetrazol-5-yl) 5-heptenamide, dihydrochloride.

67. (2S,5E)-2-amino-6-fluoro-7-[(1-iminoethyl)amino]-5-heptenoic acid, dihydrochloride, monohydrate.

68. (2S,5E/Z)-2-amino-6-fluoro-7-[(1-iminoethyl)amino]-5-heptenoic acid, dihydrochloride.

69. (2S,5Z)-2-amino-6-fluoro-7-[(1-iminoethyl)amino]-5-heptenoic acid, dihydrochloride.

70. (2S,5E/Z)-2-amino-5-fluoro-7-[(1-iminoethyl)amino]-5-heptenoic acid, dihydrochloride.

71. (2S,5E/Z)-2-amino-5-methyl-6-fluoro-7-[(1-iminoethyl)amino]-5-heptenoic acid, dihydrochloride.

72. (2R,5E)-2-amino-6-fluoro-7-[(1-iminoethyl)amino]-5-heptenoic acid, dihydrochloride, monohydrate.

73. (2S,5E/Z)-2-amino-5,6-difluoro-7-[(1-iminoethyl)amino]-5-heptenoic acid, dihydrochloride.

74. (2S,5E)-2-amino-6-fluoro-7-[(1-iminoethyl)amino]-N-(1H-tetrazol-5-yl) 5-heptenamide.

75. A method of treating or preventing an inflammation related condition in a subject in need of such treatment or prevention comprising:

administering a treatment or prevention effective amount of a compound of formula I

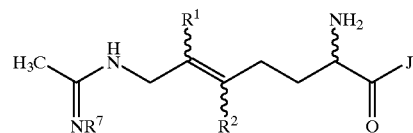

or a pharmaceutically acceptable salt thereof, wherein:
   $R^1$ is selected from the group consisting of H, halo and alkyl which is optionally substituted by one or more halo;
   $R^2$ is selected from the group consisting of H, halo and alkyl which is optionally substituted by one or more halo;
   with the proviso that at least one of $R_1$ or $R_2$ contains a halo; $R^1$ is selected from the group consisting of H, halo and alkyl which is optionally substituted by one or more halo;
   $R^2$ is selected from the group consisting of H, halo and alkyl which is optionally substituted by one or more halo;
with the proviso that at least one of $R^1$ or $R^2$ contains a halo;
   $R^7$ is selected from the group consisting of H and hydroxy; and
   J is selected from the group consisting of hydroxy, alkoxy, and $NR^3R^4$ wherein;
   $R^3$ is selected from the group consisting of H, lower alkyl, lower alkylenyl and lower alkynyl; and
   $R^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino to a subject in need of such treatment or prevention.

76. the method of claim 75 wherein said inflammation related condition is an arthritis condition.

77. the method of claim 76 wherein said arthritis condition is osteoarthritis.

78. The method of claim 76 wherein said arthritis condition is rhumatoid arthritis.

79. The method of claim 75 wherein said inflammation related condition is post-operative inflammation.

80. The method of claim 79 wherein said post-operative inflammation is associated with ophthalmic surgery.

81. The method of claim 80 wherein said ophthalmic surgery is cataract surgery.

82. The method of claim 75 wherein said inflammation related condition is associated with an infection.

83. The method of claim 82 wherein said infection is sepsis.

84. The method of claim 82 wherein said infection is caused by a virus.

85. The method of claim 75 wherein said inflammation related condition is inflammatory bowel syndrome.

86. The method of claim 75 wherein said inflammatory related condition is caused by injury.

87. The method of claim 75 wherein said inflammatory related condition is pulmonary inflammation.

88. The method of claim 87 wherein said pulmonary inflammation is caused by cystic fibrosis.

89. A method of treating or preventing a malignant neoplasia in a subject in need of such treatment or prevention comprising:

administering a treatment or prevention effective amount of a compound of formula I

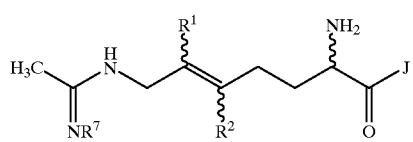

I or a pharmaceutically acceptable salt thereof, wherein:

$R^1$ is selected from the group consisting of H, halo and alkyl which is optionally substituted by one or more halo;

$R^2$ is selected from the group consisting of H, halo and alkyl which is optionally substituted by one or more halo;

with the proviso that at least one of $R_1$ or $R_2$ contains a halo; $R^1$ is selected from the group consisting of H, halo and alkyl which is optionally substituted by one or more halo;

$R^2$ is selected from the group consisting of H, halo and alkyl which is optionally substituted by one or more halo;

with the proviso that at least one of $R^1$ or $R^2$ contains a halo;

$R^7$ is selected from the group consisting of H and hydroxy; and

J is selected from the group consisting of hydroxy, alkoxy, and $NR^3R^4$ wherein;

$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino to a subject in need of such treatment or prevention.

90. The method of claim 89 wherein said cancer is an epithelial cell-derived neoplasia.

91. The method of claim 90 wherein said epithelial cell-derived neoplasia is a gastrointestinal cancer.

92. The method of claim 91 wherein said epithelial cell-derived neoplasia is colon cancer.

93. The method of claim 90 wherein said epithelial cell derived neoplasia is lung cancer.

94. The method of claim 90 wherein said epithelial cell derived neoplasia is prostate cancer.

95. The method of claim 90 wherein said epithelial cell derived neoplasia is cervical cancer.

96. The method of claim 90 wherein said epithelial cell derived neoplasia is breast cancer.

97. The method of claim 89 wherein said malignant neoplasia is mesenchymal tissue derived.

98. A method of treating addiction in a subject in need of such treatment comprising:

administering a treatment effective amount of a compound of formula I

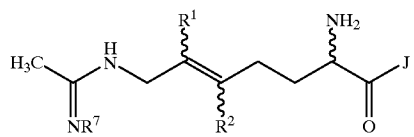

or a pharmaceutically acceptable salt thereof, wherein:

$R^1$ is selected from the group consisting of H, halo and alkyl which is optionally substituted by one or more halo;

$R^2$ is selected from the group consisting of H, halo and alkyl which is optionally substituted by one or more halo;

with the proviso that at least one of $R_1$ or $R_2$ contains a halo; $R^1$ is selected from the group consisting of H, halo and alkyl which is optionally substituted by one or more halo;

$R^2$ is selected from the group consisting of H, halo and alkyl which is optionally substituted by one or more halo; with the proviso that at least one of $R^1$ or $R^2$ contains a halo;

$R^7$ is selected from the group consisting of H and hydroxy; and

J is selected from the group consisting of hydroxy, alkoxy, and $NR^3R^4$ wherein;

$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino to a subject in need of such treatment.

99. The method of claim 98 wherein said addiction is an addiction to alcohol.

100. The method of claim 98 wherein said addiction is an addiction to nicotine.

101. A compound having the structure corresponding to Formula IV:

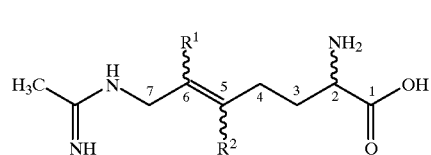

or a pharmaceutically acceptable salt thereof, wherein:

$R^1$ is selected from the group consisting of H and halo; and $R^2$ is selected from the group consisting of H, halo and alkyl which is optionally substituted by one or more halo; and with the proviso that at least one of $R^1$ or $R^2$ contains a halo.

102. The compound of claim 101 wherein:

$R^1$ is halo; and $R^2$ is selected from the group consisting of H and halo.

103. The compound of claim 101 wherein:

$R^1$ is selected from the group consisting of H and F; and $R^2$ is halo.

104. The compound of claim 101 wherein:

$R^1$ is fluorine; and $R^2$ is selected from the group consisting of H and $C_1$–$C_3$ alkyl, said $C_1$–$C_3$ alkyl optionally substituted by one or more halo.

105. The compound of claim 101 wherein:

$R^1$ is fluorine $R^2$ is H.

106. The compound of claim 101 wherein:

$R^1$ is fluorine; and $R^2$ is fluorine.

* * * * *